(12) United States Patent
Burghes et al.

(10) Patent No.: US 9,845,469 B2
(45) Date of Patent: Dec. 19, 2017

(54) ANTISENSE OLIGONUCLEOTIDES FOR TREATMENT OF SPINAL MUSCULAR ATROPHY

(71) Applicant: Ohio State Innovation Foundation, Columbus, OH (US)

(72) Inventors: Arthur Burghes, Columbus, OH (US); Vicki McGovern, Hilliard, OH (US); Thomas Prior, New Albany, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/117,758

(22) PCT Filed: Feb. 10, 2015

(86) PCT No.: PCT/US2015/015212
§ 371 (c)(1),
(2) Date: Aug. 10, 2016

(87) PCT Pub. No.: WO2015/120450
PCT Pub. Date: Aug. 13, 2015

(65) Prior Publication Data
US 2016/0355811 A1 Dec. 8, 2016

Related U.S. Application Data

(60) Provisional application No. 61/937,828, filed on Feb. 10, 2014.

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/11* (2013.01); *C12N 2310/314* (2013.01); *C12N 2310/3233* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 2006/0281701 A1* | 12/2006 | Stein | C12N 15/1131 514/44 A |
| 2009/0239932 A1* | 9/2009 | Sale | C12N 15/1135 514/44 A |
| 2010/0184947 A1* | 7/2010 | Kuik-Romeijn | A61K 47/48238 530/322 |
| 2010/0216238 A1 | 8/2010 | Baker et al. | |
| 2015/0315582 A1* | 11/2015 | Singh | C12N 15/113 514/44 A |

FOREIGN PATENT DOCUMENTS

WO    2013086207 A1    6/2013

OTHER PUBLICATIONS

Alter, J., et al., Systemic delivery of morpholino oligonucleotide restores dystrophin expression bodywide and improves dystrophic pathology, Nat. Med. (2006) 12(2):175-177.
Baughan, T.D., et al., Delivery of bifunctional RNAs that target an intronic repressor and increase SMN levels in an animal model of spinal muscular atrophy, Hum. Mol. Genet. (2009) 18(9):1600-1611.
Bebee, T.W. et al., Splicing regulation of the Survival Motor Neuron genes and implications for treatment of spinal muscular atrophy, Front. Biosci. (2011) 15:1191-1204.
Burghes, A.H. et al., Antisense oligonucleotides and spinal muscular atrophy: skipping along, Genes Dev (2010) 24:1574-1579.
Burghes, A.H. et al., Spinal muscular atrophy: why do low levels of survival motor neuron protein make motor neurons sick? Nat Rev Neurosci (2009) 10:597-609.
Burnett, B.G. et al., Regulation of SMN Protein Stability, Mol Cell Biol (2009) 29(5):1107-1115.
Cartegni, L. et al., Disruption of an SF2/ASF-dependent exonic splicing enhancer in SMN2 causes spinal muscular atrophy in the absence of SMN1, Nat Genet (2002) 30:377-384.
Cirak, S. et al., Exon skipping and dystrophin restoration in patients with Duchenne muscular dystrophy after systemic phosphorodiamidate morpholino oligomer treatment: an open-label, phase 2, dose-escalation study, Lancet (2011) 378:595-605.
Coovert, D.D. et al., The survival motor neuron protein in spinal muscular atrophy, Hum Mol Genet (1997) 6(8):1205-1214.
Ellet, F. et al., Zebrafish as a model for vertebrate hematopoiesis, Curr. Opin. Pharmacol. (2010) 10:563-570.
Feldkotter, M. et al., Quantitative Analyses of SMN1 and SMN2 Based on Real-Time LightCycler PCR: Fast and Highly Reliable Carrier Testing and Prediction of Severity of Spinal Muscular Atrophy, Am J Hum Genet 2002) 70:358-368.
Foust, Kevin D. et al., Rescue of the spinal muscular atrophy phenotype in a mouse model by early postnatal delivery of SMN, Nature Biotech. (2010) 28(3):271-274.
Gallo, M. et al., 2'-C-Methyluridine phosphoramidite: a new building block for the preparation of RNA analogues carrying the 2'-hydroxyl group, Tetrahedron (2001) 57:5707-5713.
Gavrilina, T.O. et al., Neuronal SMN expression corrects spinal muscular atrophy in severe SMA mice while muscle-specific SMN expression has no phenotypic effect, Hum. Mol. Genet. (2008) 17(8):1063-1075.
Gennarelli, M. et al., Survival Motor Neuron Gene Transcript Analysis in Muscles from Spinal Muscular Atrophy Patients, Biochem Biophys Res Commun (1995) 213(1):342-348.
(Continued)

*Primary Examiner* — Tracy Vivlemore
(74) *Attorney, Agent, or Firm* — Wood Herron & Evans LLP

(57) ABSTRACT

Various aspects of the present invention are directed to compounds targeted to various regions of the survival motor neuron 2 (SMN2) gene. Such compounds may be used to increase incorporation of exon 7 in processed transcripts of SMN2. Such compounds may therefore be useful in increasing the amount of full-length SMN protein produced by the SMN2 gene. As such, these compounds may provide a therapeutic approach for treatment of spinal muscular atrophy (SMA).

15 Claims, 9 Drawing Sheets

(56) References Cited

OTHER PUBLICATIONS

Hovhannisyan, R.H. et al., A Novel Intronic cis Element, ISE/ISS-3, Regulates Rat Fibroblast Growth Factor Receptor 2 Splicing through Activation of an Upstream Exon and Repression of a Downstream Exon Containing a Noncanonical Branch Point Sequence, Mol. Cell. Biol. (2005) 25(1):250-263.

Hsieh-Li, H.M. et al., A mouse model for spinal muscular atrophy, Nat. Genet. (2000) 24:66-70.

Hua, Y. et al., Antisense correction of SMN2 splicing in the CNS rescues necrosis in a type III SMA mouse model, Genes Dev. (2010) 24:1634-1644.

Hua, Y. et al., Antisense Masking of an hnRNP A1/A2 Intronic Splicing Silencer Corrects SMN2 Splicing in Transgenic Mice, Am. J. Hum. Genet. (2008) 82:834-848.

Hua, Y. et al., Enhancement of SMN2 Exon 7 Inclusion by Antisense Oligonucleotides Targeting the Exon, PLoS Biol (2007) 5(4)e73:0729-0744.

Hua, Y. et al., Peripheral SMN restoration is essential for long-term rescue of a severe spinal muscular atrophy mouse model, Nature (2011) 478:123-126.

International Search Report in International Patent Application No. PCT/US2015/15212, dated May 20, 2015, 1 pg.

Järver, P. et al., Peptide-mediated Cell and In Vivo Delivery of Antisense Oligonucleotides and siRNA, Mol Ther Nucleic Acids (2012) 1(e27):1-17.

Kashima, T. et al., A negative element in SMN2 exon 7 inhibits splicing in spinal muscular atrophy, Nat. Genet. (2003) 34(4) 460-463.

Kashima, T. et al., An intronic element contributes to splicing repression in spinal muscular atrophy, Proc Natl Acad Sci (2007) 104(9):3426-3431.

Kinali, M. et al., Local restoration of dystrophin expression with the morpholino oligomer AVI-4658 in Duchenne muscular dystrophy: a single-blind, placebo-controlled, dose-escalation, proof-of-concept study, Lancet Neurol (2009) 8:918-928.

Le, T.T. et al., SMNDelta7, the major product of the centromeric survival motor neuron (SMN2) gene, extends survival in mice with spinal muscular atrophy and associates with full-length SMN. Hum. Mol. Genet. (2005) 14(6):845-857.

Le, T.T. et al., Temporal requirement for high SMN expression in SMA mice, Hum. Mol. Genet. (2011) 20:3578-3591.

Lefebvre, S. et al., Correlation between severity and SMN protein level in spinal muscular atrophy. Nat Genet (1997) 16:265-269.

Lefebvre, S. et al., Identification and Characterization of a Spinal Muscular Atrophy-Determining Gene, Cell (1995) 80:155-165.

Lorson, C.L. et al., A single nucleotide in the SMN gene regulates splicing and is responsible for spinal muscular atrophy. Proc Natl Acad Sci USA (1999) 96:6307-6311.

Lorson, C.L. et al., An exonic enhancer is required for inclusion of an essential exon in the SMA-determining gene SMN, Hum Mol Genet (2000) 9(2):259-265.

Lorson, C.L. et al., SMN oligomerization defect correlates with spinal muscular atrophy severity, Nat Genet (1998) 19:63-66.

Mailman, M.D. et al., Molecular analysis of spinal muscular atrophy and modification of the phenotype by SMN2, Genet Med (2002) 4(1):20-26.

McAndrew, P.E. et al., Identification of Proximal Spinal Muscular Atrophy Carriers and Patients by Analysis of SMNT and SMNC Gene Copy Number, Am J Hum Genet (1997) 60:1411-1422.

Meyer, K. et al., Improving Single Injection CSF Delivery of AAV9-mediated Gene Therapy for SMA: A Dose-response Study in Mice and Nonhuman Primates, Molecul Ther (Oct. 31, 2014) I doi:10. 1038/mt.2014.210.

Minovitsky, S. et al.. The splicing regulartory element, UGCAUG, is phylogenetically and spatially conserved in introns that flank tissue-specific alternative exons, Nucleic Acids Res. (2005) 33(2):714-724.

Monani, U.R. et al., A single nucleotide difference that alters splicing patterns distinguishes the SMA gene SMN1 from the copy gene SMN2, Hum Mol Genet (1999) 8(7):1177-1183.

Monani, U.R. et al., The human centromeric survival motor neuron gene (SMN2) rescues embryonic lethality in Smn (−/−) mice and results in a mouse with spinal muscular atrophy, Hum Mol Genet (2000) 9(3):333-339.

Morcos, P.A., Achieving targeted and quantifiable alteration of mRNA splicing with Morpholino oligos, Biochem. Biophys. Res. Commun. (2007) 358:521-527.

Parsons, D.W. et al., An 11 base pair duplication in exon 6 of the SMN gene produces a type I spinal muscular atrophy (SMA) phenotype: further evidence for SMN as the primary SMA-determining gene, Hum Mol Genet (1996) 5(11):1727-1732.

Passini, M.A. et al., Antisense Oligonucleotides Delivered to the Mouse CNS Ameliorate Symptoms of Severe Spinal Muscular Atrophy, Sci Transl Med (2011) 3(72) 72ra18.

Passini, M.A., et al., CNS-targeted gene therapy improves survival and motor function in a mouse model of spinal muscular atrophy, J. Clin. Invest. (2010) 120(4):1253-1264.

Porensky, P.N. et al., A single administration of morpholino antisense oligomer rescues spinal muscular atrophy in mouse, Hum Mol Genet (2012) 21(7):1625-1638.

Prior, T.W. et al., A Positive Modifier of Spinal Muscular Atrophy in the SMN2 Gene, Am J Hum Genet (2009) 85:408-413.

Sazani, P., et al., Repeat-Dose Toxicology Evaluation in Cynomolgus Monkeys of AVI-4658, a Phosphorodiamidate Morpholino Oligomer (PMO) Drug for the Treatment of Duchenne Muscular Dystrophy, Int. J. Toxicol. (2011) 30(3):313-321.

Scamborova, P. et al., An Intronic Enhancer Regulates Splicing of the Twintron of *Drosophila melanogaster prospero* Pre-mRNA by Two Different Spliceosomes, Mol. Cell. Biol. (2004) 24(5):1855-1869.

Scaringe, S., RNA Oligonucelotide Synthesis via 5'-Silyl-2'-Orthoester Chemistry, Methods (2001), 23:206-217.

Schrank, B. et al., Inactivation of the survival motor neuron gene, a candidate gene for human spinal muscular atrophy, leads to massive cell death in early mouse embryos, Proc. Natl. Acad. Sci. USA (1997) 94:9920-9925.

Singh, N.K. et al., Splicing of a Critical Exon of Human Survival Motor Neuron is Regulated by a Unique Silencer Element Located in the Last Intron, Mol. Cell Biol. (2006) 26:1333-1346.

Singh, N.N. et al., An intronic structure enabled by a long-distance interaction serves as a novel target for splicing correction in spinal muscular atrophy, Nucleic Acids Res (2013) 41(17):8144-8165.

Williams, J.H. et al., Oligonucleotide-Mediated Survival of Motor Neuron Protein Expression in CNS Improves Phenotype in a Mouse Model of Spinal Muscular Atrophy, J. Neurosci. (2009) 29(4):7633-7638.

Wilton, S.D. et al., Specific removal of the nonsense mutation from the mdx dystrophin mRNA using antisense oligonucleotides, Neuromuscul. Disord. (1999) 9:330-338.

Written Opinion in International Patent Application No. PCT/US2015/15212, dated May 20, 2015, 5 pgs.

Wu, B. et al., One-year Treatment of Morpholino Antisense Oligomer Improves Skeletal and Cardiac Muscle Functions in Dystrophic mdx Mice, Mol. Ther. (2011) 19(3):576-583.

Yeo, G. et al., Variation in sequence and organization of splicing regulatory elements in vertebrate genes, Proc. Natl. Acad. Sci. U.S.A. (2004) 101(44):15700-15705.

Yokota, T. et al., Efficacy of Systemic Morpholino Exon-Skipping in Duchenne Dystrophy Dogs, Ann. Neurol. (2009) 65:667-676.

\* cited by examiner

SEQUENCE LISTING

<160> NUMBER OF SEQ ID NOS: 28

<210> SEQ ID NO 1
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 1
aagtctgcag gtctgcctac tagtg                25

<210> SEQ ID NO 2
<211> LENGTH: 25
<212> TYPE: DNA
<213> ORGANISM: Artificial Sequence
<220> FEATURE:
<223> OTHER INFORMATION: ANTISENSE COMPOUND

```
<400> SEQUENCE: 2
aagtctgcag gtcagcctac tagtg                                      25

<210> SEQ ID NO 3
<211> LENGTH: 20
<212> TYPE: DNA
<213> ORGANISM: Artificial Sequence
<220> FEATURE:
<223> OTHER INFORMATION: ANTISENSE COMPOUND

<400> SEQUENCE: 3
aagtctgctg gtctgcctac                                            20

<210> SEQ ID NO 4
<211> LENGTH: 23
<212> TYPE: DNA
<213> ORGANISM: Artificial Sequence
<220> FEATURE:
<223> OTHER INFORMATION: ANTISENSE COMPOUND

<400> SEQUENCE: 4
gttttccaca aaccagcaga ctt                                        23

<210> SEQ ID NO 5
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 5
ttcaactttc taacatctga acttt                                      25

<210> SEQ ID NO 6
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 6
ctagtaggga tgtagattaa ccttt                                      25

<210> SEQ ID NO 7
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 7
ctaacatctg caaaccagca gactt                                      25

<210> SEQ ID NO 8
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 8
cttccacaca accaaccagt taagt                                      25

<210> SEQ ID NO 9
```

```
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 9
ctagtaggtc aaaccatgca gactt                                          25

<210> SEQ ID NO 10
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 10
gcgtggtggc tcaggctagg cacag                                          25

<210> SEQ ID NO 11
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 11
tagctatata gacatagata gctat                                          25

<210> SEQ ID NO 12
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 12
atagacatag atttggctca ggcta                                          25

<210> SEQ ID NO 13
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 13
atgtgagcac cttccttctt tttga                                          25

<210> SEQ ID NO 14
<211> LENGTH: 15
<212> TYPE: DNA
<213> ORGANISM: Artificial Sequence
<220> FEATURE:
<223> OTHER INFORMATION: ANTISENSE COMPOUND

<400> SEQUENCE: 14
atttaaggaa tgtga                                                     15

<210> SEQ ID NO 15
<211> LENGTH: 20
<212> TYPE: DNA
<213> ORGANISM: Artificial Sequence
<220> FEATURE:
<223> OTHER INFORMATION: ANTISENSE COMPOUND

<400> SEQUENCE: 15
```

```
tttttgattt tgtctaaaac                                                    20

<210> SEQ ID NO 16
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 16
aaggaatgtg atttttgat tttgt                                               25

<210> SEQ ID NO 17
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 17
aaggaatgtg attgattttg tctaa                                              25

<210> SEQ ID NO 18
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 18
ctttctaaca tctgaacttt ttaaa                                              25

<210> SEQ ID NO 19
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 19
cctttcaact ttctaacatc tgaac                                              25

<210> SEQ ID NO 20
<211> LENGTH: 25
<212> TYPE: DNA
<213> ORGANISM: Artificial Sequence
<220> FEATURE:
<223> OTHER INFORMATION: ANTISENSE COMPOUND

<400> SEQUENCE: 20
attaaccttt caactttcta acatc                                              25

<210> SEQ ID NO 21
<211> LENGTH: 29
<212> TYPE: DNA
<213> ORGANISM: Artificial Sequence
<220> FEATURE:
<223> OTHER INFORMATION: PRIMER

<400> SEQUENCE: 21
ttatatactt ttaaacatat agaagatag                                          29

<210> SEQ ID NO 22
<211> LENGTH: 24
<212> TYPE: DNA
```

```
<213> ORGANISM: Artificial Sequence
<220> FEATURE:
<223> OTHER INFORMATION: PRIMER

<400> SEQUENCE: 22
agattctctt gatgatgctg aatg                                          24

<210> SEQ ID NO 23
<211> LENGTH: 26
<212> TYPE: DNA
<213> ORGANISM: Artificial Sequence
<220> FEATURE:
<223> OTHER INFORMATION: PRIMER

<400> SEQUENCE: 23
gtttcagaca aaatcaaaaa gaagga                                        26

<210> SEQ ID NO 24
<211> LENGTH: 26
<212> TYPE: DNA
<213> ORGANISM: Artificial Sequence
<220> FEATURE:
<223> OTHER INFORMATION: PRIMER

<400> SEQUENCE: 24
tctataacgc ttcacattcc agatct                                        26

<210> SEQ ID NO 25
<211> LENGTH: 27
<212> TYPE: DNA
<213> ORGANISM: Artificial Sequence
<220> FEATURE:
<223> OTHER INFORMATION: PROBE

<400> SEQUENCE: 25
atgccagcat ttctccttaa tttaagg                                       27

<210> SEQ ID NO 26
<211> LENGTH: 20
<212> TYPE: DNA
<213> ORGANISM: Artificial Sequence
<220> FEATURE:
<223> OTHER INFORMATION: PRIMER

<400> SEQUENCE: 26
gtcaacccca ccgtgttctt                                               20

<210> SEQ ID NO 27
<211> LENGTH: 21
<212> TYPE: DNA
<213> ORGANISM: Artificial Sequence
<220> FEATURE:
<223> OTHER INFORMATION: PRIMER

<400> SEQUENCE: 27
ttggaacttt gtctgcaaac a                                             21

<210> SEQ ID NO 28
<211> LENGTH: 14
<212> TYPE: DNA
<213> ORGANISM: Artificial Sequence
<220> FEATURE:
```

```
<223> OTHER INFORMATION: PROBE

<400> SEQUENCE: 28
cttgggccgc gtct                                                         14
```

ANTISENSE OLIGONUCLEOTIDES FOR TREATMENT OF SPINAL MUSCULAR ATROPHY

CROSS-REFERENCE TO RELATED APPLICATIONS

This application claims priority to, and the benefit of the filing date of, U.S. Patent Application Ser. No. 61/937,828, entitled "Antisense Oligonucleotides for Treatment of Spinal Muscular Atrophy," filed on Feb. 10, 2014, the disclosure of which is incorporated by reference herein in its entirety.

FIELD OF THE INVENTION

The present invention relates generally to antisense oligonucleotides that are useful in the treatment of spinal muscular atrophy, and more specifically to antisense oligonucleotides that can enhance the production of full-length survival motor neuron (SMN) protein.

BACKGROUND

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Spinal muscular atrophy (SMA) is an autosomal recessive disease caused by a genetic defect in the SMN1 gene, which encodes survival motor neuron (SMN) protein, which is widely expressed in eukaryotic cells. SMN protein is critical to the function of the nerves that control muscles (the motor neurons). Diminished abundance of the protein results in loss of function of neuronal cells in the anterior horn of the spinal cord and subsequent system-wide muscle atrophy. The condition is debilitating and often fatal.

A second gene also has a role in producing SMN protein. This is the survival motor neuron 2 gene (SMN2), often called the SMA "back-up gene." However, most of the SMN protein produced by SMN2 lacks a key building block that is normally produced by SMN1. This means that SMN2 cannot fully make up for the mutated SMN1 gene.

Thus, spinal muscular atrophy is caused by loss or mutation of the SMN1 gene and retention of the SMN2 gene [Lefebvre, S., Burglen, L., Reboullet, S., Clermont, O., Burlet, P., Viollet, L., Benichou, B., Cruaud, C., Millasseau, P., Zeviani, M. et al. (1995) *Identification and characterization of a spinal muscular atrophy-determining gene.* Cell, 80, 155-165; Burghes, A. H. and Beattie, C. E. (2009) *Spinal muscular atrophy: why do low levels of survival motor neuron protein make motor neurons sick?* Nat Rev Neurosci, 10, 597-609]. As has been described, the SMN2 gene differs from the SMN1 gene by a single nucleotide, which disrupts a splice modulator in exon 7 in SMN2 [Lorson, C. L., Hahnen, E., Androphy, E. J. and Wirth, B. (1999) *A single nucleotide in the SMN gene regulates splicing and is responsible for spinal muscular atrophy.* Proc Natl Acad Sci USA, 96, 6307-6311; Monani, U. R., Lorson, C. L., Parsons, D. W., Prior, T. W., Androphy, E. J., Burghes, A. H. and McPherson, J. D. (1999) *A single nucleotide difference that alters splicing patterns distinguishes the SMA gene SMN*1 *from the copy gene SMN*2. Hum Mol Genet, 8, 1177-1183; Cartegni, L. and Krainer, A. R. (2002) *Disruption of an SF2/ASF-dependent exonic splicing enhancer in SMN2 causes spinal muscular atrophy in the absence of SMN*1. Nat Genet, 30, 377-384; Kashima, T. and Manley, J. L. (2003) *A negative element in SMN2 exon 7 inhibits splicing in spinal muscular atrophy.* Nat Genet, 34, 460-463]. The disruption of this splice modulator results in the majority of the transcript from SMN2 lacking exon 7 and, in turn, the SMN protein lacking exon 7 does not self-associate readily and is rapidly degraded [Gennarelli, M., Lucarelli, M., Capon, F., Pizzuti, A., Merlini, L., Angelini, C., Novelli, G. and Dallapiccola, B. (1995) *Survival motor neuron gene transcript analysis in muscles from spinal muscular atrophy patients.* Biochem Biophys Res Commun, 213, 342-348; Parsons, D. W., McAndrew, P. E., Monani, U. R., Mendell, J. R., Burghes, A. H. and Prior, T. W. (1996) *An 11 base pair duplication in exon 6 of the SMN gene produces a type I spinal muscular atrophy (SMA) phenotype: further evidence for SMN as the primary SMA-determining gene.* Hum Mol Genet, 5, 1727-1732; Lefebvre, S., Burlet, P., Liu, Q., Bertrandy, S., Clermont, O., Munnich, A., Dreyfuss, G. and Melki, J. (1997) *Correlation between severity and SMN protein level in spinal muscular atrophy.* Nat Genet, 16, 265-269; Coovert, D. D., Le, T. T., McAndrew, P. E., Strasswimmer, J., Crawford, T. O., Mendell, J. R., Coulson, S. E., Androphy, E. J., Prior, T. W. and Burghes, A. H. (1997) *The survival motor neuron protein in spinal muscular atrophy.* Hum Mol Genet, 6, 1205-1214; Lorson, C. L. and Androphy, E. J. (2000) *An exonic enhancer is required for inclusion of an essential exon in the SMA-determining gene SMN.* Hum Mol Genet, 9, 259-265; Lorson, C. L., Strasswimmer, J., Yao, J. M., Baleja, J. D., Hahnen, E., Wirth, B., Le, T., Burghes, A. H. and Androphy, E. J. (1998) *SMN oligomerization defect correlates with spinal muscular atrophy severity.* Nat Genet, 19, 63-66; Burnett, B. G., Munoz, E., Tandon, A., Kwon, D. Y., Sumner, C. J. and Fischbeck, K. H. (2009) *Regulation of SMN protein stability.* Mol Cell Biol, 29, 1107-1115]. This results in less SMN protein and SMA.

More specifically, human chromosome 5 contains two nearly identical genes at location 5q13: a telomeric copy SMN1 and a centromeric copy SMN2. In healthy individuals, the SMN1 gene codes the survival of motor neuron protein (SMN) which, as its name says, plays a crucial role in survival of motor neurons. The SMN2 gene, on the other hand—due to a variation in a single nucleotide (840.C→T)—undergoes alternative splicing at the junction of intron 6 to exon 8, with only 10-20% of SMN2 transcripts coding a fully functional survival of motor neuron protein (SMN-fl) and 80-90% of transcripts resulting in a truncated protein compound (SMNΔ7) which is rapidly degraded in the cell.

In individuals affected by SMA, the SMN1 gene is mutated in such a way that it is unable to correctly code the SMN protein—due to either a deletion occurring at exon 7 or to other point mutations (frequently resulting in the functional conversion of the SMN1 sequence into SMN2). All patients, however, retain at least one copy of the SMN2 gene (with most having 2-4 of them) which still codes small amounts of SMN protein—around 10-20% of the normal level—allowing some neurons to survive. In the long run, however, reduced availability of the SMN protein results in gradual death of motor neuron cells in the anterior horn of spinal cord and the brain. Muscles that depend on these motor neurons for neural input now have decreased innervation (also called denervation), and therefore have decreased input from the central nervous system (CNS).

Denervated skeletal muscle is more difficult for the body to control. Decreased impulse transmission through the motor neurons leads to decreased contractile activity of the denervated muscle. Consequently, denervated muscles undergo progressive atrophy.

Spinal muscular atrophy manifests in various degrees of severity, which all have in common progressive muscle wasting and mobility impairment. Proximal muscles and lung muscles are affected first. Other body systems may be affected as well, particularly in early-onset forms. SMA is the most common genetic cause of infant death.

The copy number of SMN2 inversely correlates with patient severity and increased full-length SMN from an SMN2 gene also correlates with a milder phenotype [McAndrew, P. E., Parsons, D. W., Simard, L. R., Rochette, C., Ray, P. N., Mendell, J. R., Prior, T. W. and Burghes, A. H. (1997) *Identification of proximal spinal muscular atrophy carriers and patients by analysis of SMNT and SMNC gene copy number*. Am J Hum Genet, 60, 1411-1422; Mailman, M. D., Heinz, J. W., Papp, A. C., Snyder, P. J., Sedra, M. S., Wirth, B., Burghes, A. H. and Prior, T. W. (2002) *Molecular analysis of spinal muscular atrophy and modification of the phenotype by SMN2*. Genet Med, 4, 20-26; Feldkotter, M., Schwarzer, V., Wirth, R., Wienker, T. F. and Wirth, B. (2002) *Quantitative analyses of SMN1 and SMN2 based on real-time lightCycler PCR: fast and highly reliable carrier testing and prediction of severity of spinal muscular atrophy*. Am J Hum Genet, 70, 358-368; Prior, T. W., Krainer, A. R., Hua, Y., Swoboda, K. J., Snyder, P. C., Bridgeman, S. J., Burghes, A. H. and Kissel, J. T. (2009) *A positive modifier of spinal muscular atrophy in the SMN2 gene*. Am J Hum Genet, 85, 408-413]. The severity of SMA symptoms is broadly related to how well the remaining SMN2 genes can make up for the loss of SMN1. This is partly related to the number of SMN2 gene copies present on the chromosome. Patients with SMA can have between 1 and 4 (or more) copies, with the greater the number of SMN2 copies, the milder the disease severity. Thus, most SMA type I patients have one or two SMN2 copies; SMA II and III patients usually have at least three SMN2 copies; and SMA IV patients normally have at least four of them.

Generally, patients tend to deteriorate over time, but prognosis varies with the SMA type and disease progress which is most rapid in SMN type I.

The majority of children diagnosed with SMA type 0/I do not reach the age of 2 without respiratory intervention— recurrent respiratory problems being the primary cause of morbidity. With proper care, milder SMA type II and III cases live into adulthood.

In SMA type II, the course of the disease is stable or slowly progressing and life expectancy is reduced compared to the healthy population. Death before the age of 20 is frequent, although many patients live to become parents and grandparents.

SMA type III has near-normal life expectancy if standards of care are followed. Adult-onset SMA usually means only mobility impairment and does not affect life expectancy.

Thus increasing, enhancing, and/or restoring SMN levels should have a beneficial impact on the SMA phenotype in a subject (e.g., humans).

There is no known cure for spinal muscular atrophy. And so, care largely involves treating the symptoms of SMA (e.g., palliative care). However, since the underlying genetic mechanism of SMA was described in 1990, several therapeutic approaches have been proposed and investigated. Since a vast number of in vitro and animal modelling studies suggest that restoration of SMN levels reverts SMA symptoms, the majority of emerging therapies focus on increasing the availability of SMN protein to motor neurons. Such therapeutic pathways include gene replacement and SMN2 gene conversion.

Gene therapy aims at correcting the SMN1 gene function through inserting specially crafted nucleotide sequences with the help of a viral vector. In the context of SMA, it is currently being researched using the scAAV9 viral vector at the Ohio State University and Nationwide Children's Hospital, USA, and the University of Sheffield, United Kingdom, as well as by Genzyme Corporation, USA, and Généthon, France. In one study this method has resulted in the greatest survival increase achieved to-date in a SMNΔ7 mouse model (median survival of 400 days in treated mice as opposed to 15 days in untreated mice) [Foust, Nature Biotech. 28, 271-274 (2010)]. Safety and pharmacokinetics of scAAV9 viral vector has been tested in non-human primates [Meyer, Molecul Ther (31 Oct. 2014) I doi:10.1038/mt.2014.210]. An AAV9 viral vector is in clinical trials for Hemophilia B. scAAV9-SMN is in clinical trials currently at NCH Clinical Trials.gov Identifier: NCT02122952.

SMN2 gene conversion, also known as 'SMN2' alternative splicing modulation, essentially aims at converting the "backup" SMN2 gene (which normally produces only a fraction of needed SMN protein) into a fully functional SMN1 gene so as it is able to code for high quantities of full-length SMN protein.

Antisense therapy is a form of treatment for genetic disorders or infections. When the genetic sequence of a particular gene is known to be causative of a particular disease, it is possible to synthesize a strand of nucleic acid (DNA, RNA or a chemical analogue) that will bind to the messenger RNA (mRNA) produced by that gene and inactivate it, effectively turning that gene "off". This is because mRNA has to be single stranded for it to be translated. Alternatively, the strand might be targeted to bind a splicing site on pre-mRNA and modify the exon content of an mRNA.

This synthesized nucleic acid is termed an "anti-sense" oligonucleotide because its base sequence is complementary to the gene's messenger RNA (mRNA), which is called the "sense" sequence (so that a sense segment of mRNA "5'-AAGGUC-3'" would be blocked by the anti-sense mRNA segment "3'-UUCCAG-5'").

However, to date, no truly effective therapy has been developed (i.e., one which produces enough full length SMN protein to eliminate the effects of SMA, cure SMA, and/or result in extended survival times and rates.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

Various aspects of the present invention are directed to compounds targeted to various regions of the SMN2 gene. Such compounds may be used to increase incorporation of exon 7 in processed transcripts of SMN2. Such compounds may therefore be useful in increasing the amount of full-length SMN protein produced by the SMN2 gene. As such, these compounds may provide a therapeutic approach for treatment of SMA.

More specifically, aspects of the present invention are directed to antisense (ASO) compounds targeted to and hybridizable with a nucleic acid molecule encoding SMN2. Certain embodiments may include antisense compounds targeted to intron 6, exon 7, or intron 7 of SMN2, which modulate splicing of SMN2 pre-mRNAs. In one embodiment, modulation of splicing results in an increase in exon 7 inclusion. In certain embodiments, the antisense compounds, which may be targeted to intron 6, exon 7 or intron 7 of SMN2, are morpholino (MO) oligomers. As is generally known to those of ordinary skill in the art, and as used herein, a "morpholino" or "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen (a morpholino ring) with coupling through the ring nitrogen. The nucleic acid bases in a morpholino oligomer are bound to morpholine rings instead of deoxyribose rings and linked through phosphorodiamidate groups instead of phosphates.

In one aspect of the invention, the antisense compounds are targeted to cis splicing regulatory elements. Regulatory elements include exonic splicing enhancers (ESE), exonic splicing silencers (ESS), intronic splicing enhancers (ISE), and intronic splicing silencers (ISS). Also provided are methods for modulating splicing of SMN2 mRNA in a cell, tissue or organ using one or more of the compounds of the invention. In one aspect, the compound is targeted to an intronic splicing silencer (ISS) element. In another aspect, the compound is targeted to an exonic splicing silencer (ESS) element.

Also provided are pharmaceutical compositions comprising one or more of the compounds of the invention. Use of an antisense oligonucleotide provided herein for the preparation of a medicament for modulating splicing of an SMN2 pre-mRNA is also provided. In one aspect, modulation of splicing results in an increase in exon 7 inclusion. Use of an antisense oligonucleotide provided herein for the preparation of a medicament for the treatment of spinal muscular atrophy is further provided.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION

Figure 1:
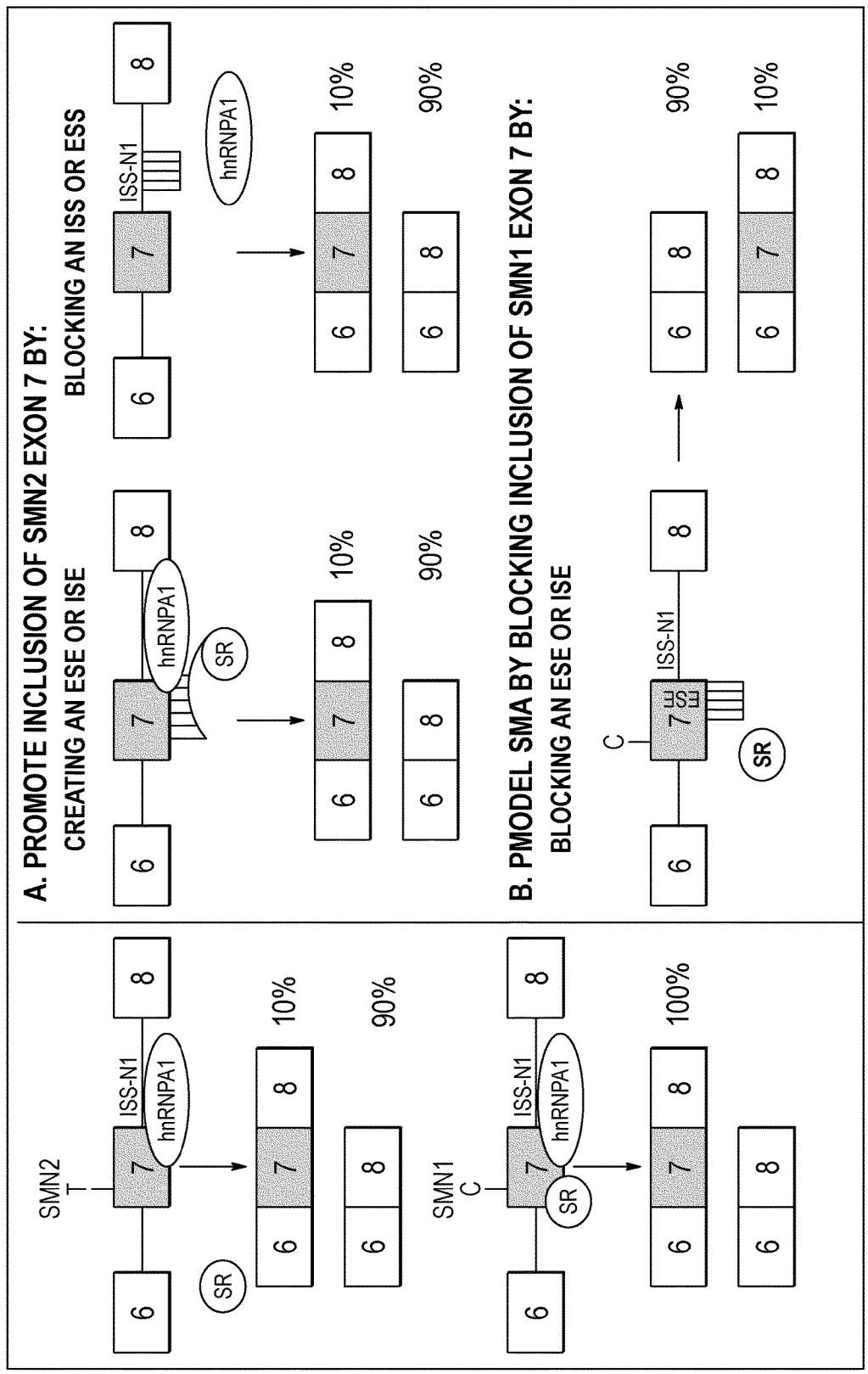
FIG. 1 is a schematic of a portion of the SMN2 gene.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described above, disclosed herein are oligomeric compounds, including antisense oligonucleotides and other antisense compounds for use in modulating the expression of nucleic acid molecules encoding SMN2. In one aspect of the present invention, this is accomplished by providing oligomeric compounds which hybridize with one or more target nucleic acid molecules encoding SMN2. As used herein, the terms "target nucleic acid" and "nucleic acid molecule encoding SMN2" encompass DNA encoding SMN2, RNA (including pre-mRNA and mRNA or portions thereof) transcribed from such DNA, and cDNA derived from such RNA. The oligomeric compounds disclosed herein may be used to increase incorporation of exon 7 in processed transcripts of nucleic acid molecules encoding SMN2. Such compounds may therefore be useful in increasing the amount of full-length SMN protein expressed by the SMN2 gene. As such, these compounds may also (in other aspects of the present invention) provide a therapeutic approach for treatment of SMA.

More specifically, certain aspects of the present invention are directed to antisense (ASO) compounds targeted to and hybridizable with a nucleic acid molecule encoding SMN2. Certain embodiments may include antisense compounds targeted to intron 6, intron 7, and/or exon 7 of SMN2, these antisense compounds modulating splicing of SMN2 pre-mRNAs. In one embodiment, modulation of splicing results in an increase in exon 7 inclusion. As used herein then, modulation of splicing refers to altering the processing of a pre-mRNA transcript such that the spliced mRNA molecule contains either a different combination of exons as a result of, for example, exon inclusion, or an additional sequence not normally found in the spliced mRNA, for example, an intron sequence. In the context of the present invention, modulation of splicing may refer to altering splicing of SMN2 pre-mRNA to achieve exon skipping or exon inclusion. In one embodiment, exon inclusion results in an SMN2 mRNA transcript containing exon 7.

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. An "antisense compound" or "antisense oligomeric compound" refers to an oligomeric compound that is at least partially complementary to the region of a nucleic acid molecule to which it hybridizes and which modulates its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Nonlimiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

In certain embodiments, the antisense compounds, which may be targeted to intron 6, exon 7 or intron 7 of SMN2, are morpholino (MO) oligomers. As is generally known to those of ordinary skill in the art, and as used herein, a "morpholino" or "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen (a morpholino ring) with coupling through the ring nitrogen. The nucleic acid bases in a morpholino oligomer are bound to morpholine rings instead of deoxyribose rings and linked through phosphorodiamidate groups instead of phosphates.

The compounds described herein, whether morpholino ASOs or other oligomeric compounds, are hybridizable to the target nucleic acid.

In one embodiment of the present invention, the antisense compounds are targeted to cis splicing regulatory elements. Such regulatory elements may include exonic splicing enhancers (ESE), exonic splicing silencers (ESS), intronic splicing enhancers (ISE), and intronic splicing silencers (ISS). As is known to those of ordinary skill in the art, newly synthesized eukaryotic mRNA molecules, also known as primary transcripts or pre-mRNA, made in the nucleus, are processed before or during transport to the cytoplasm for translation. Processing of the pre-mRNAs includes addition of a 5' methylated cap and an approximately 200-250 base poly(A) tail to the 3' end of the transcript.

The next step in mRNA processing is splicing of the pre-mRNA, which occurs in the maturation of most mammalian mRNAs. Introns are regions of a primary transcript (or the DNA encoding it) that are not included in the coding sequence of the mature mRNA. Exons are regions of a primary transcript that remain in the mature mRNA when it reaches the cytoplasm. The exons are spliced together to form the mature mRNA sequence.

In splicing, the 3' end of an upstream exon is joined to the 5' end of the downstream exon. Thus the unspliced RNA (or pre-mRNA) has an exon/intron junction at the 5' end of an intron and an intron/exon junction at the 3' end of an intron. After the intron is removed, the exons are contiguous at the exon/exon junction in the mature mRNA. Cryptic splice sites are those which are less often used but may be used when the usual splice site is blocked or unavailable. Alternative splicing, defined as the splicing together of different combinations of exons, may result in multiple mRNA transcripts from a single gene. As is generally known, the introns may be removed from pre-mRNA via a spliceosome, which is assembled from snRNAs and protein complexes.

Thus, processing of eukaryotic pre-mRNAs is a complex process that requires a multitude of signals and protein factors to achieve appropriate mRNA splicing. Exon definition by the spliceosome requires more than the canonical splicing signals that define intron-exon boundaries. One such additional signal is provided by cis-acting regulatory enhancer and silencer sequences, such as the exonic splicing enhancers, exonic splicing silencers, intronic splicing enhancers, and intron splicing silencers mentioned above. Certain of these regulatory sequences have been identified which either repress or enhance usage of splice donor sites or splice acceptor sites, depending on their site and mode of action (Yeo et al. 2004, Proc. Natl. Acad. Sci. U.S.A. 101(44):15700-15705). Further, binding of specific proteins (e.g., trans factors) to these regulatory sequences directs the splicing process, by promoting or inhibiting usage of particular splice sites, and thus modulates the ratio of splicing products (Scamborova et al. 2004, Mol. Cell. Biol. 24(5): 1855-1869; Hovhannisyan and Carstens, 2005, Mol. Cell. Biol. 25(1):250-263; Minovitsky et al. 2005, Nucleic Acids Res. 33(2):714-724).

And so, certain aspects of the present invention also provide methods for modulating splicing of SMN2 mRNA in a cell, tissue or organ using one or more of the compounds of the invention. In one embodiment, modulation of splicing is exon inclusion. In one aspect, the compound is targeted to an intronic splicing silencer element. In another aspect, the compound is targeted to an exonic splicing silencer element.

Thus, aspects of the present invention are based on principles of antisense technology by providing antisense oligonucleotides as the oligomeric compounds to modulate the expression of one or more specific gene products. The antisense compounds described herein may be useful for modulating gene expression via antisense mechanisms of action, including antisense mechanisms based on target occupancy. In one aspect, the antisense compounds provided herein modulate splicing of a target gene to promote exon inclusion, e.g., in certain embodiments inclusion of exon 7 of the SMN2 gene. This may be accomplished via the pairing (e.g., hybridization) of complementary strands of antisense compounds to their target sequence. An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

"Complementarity," as used herein, can refer to pairing between an antisense compound and its target. An antisense compound and a nucleic acid target (DNA or RNA) are complementary to each other when a sufficient number of complementary positions in each molecule are occupied by nucleobases which can hydrogen bond with each other. Thus, "hybridizable" and "complementary" are terms which are used to indicate a sufficient degree of precise pairing or complementarity over a sufficient number of nucleobases such that stable and specific binding occurs between the antisense compound and a target nucleic acid. However, those of ordinary skill in the art will recognize that the inclusion of mismatches between an antisense compound and a target nucleic acid is possible without eliminating the activity of the antisense compound. In other words, there need not be 100% complementarity between all bases of the antisense compound and the target nucleic acid. Thus, antisense compounds used in various aspects of the present invention may include a certain percentage of mismatches. For example, 20% of the nucleotides may be mismatched. Alternatively, the compounds may contain no more than about 15%, or no more than about 10%, or no more than about 5% mismatches. Alternatively still, the antisense compounds may contain no mismatches.

It is further understood by those of ordinary skill in the art that incorporation of nucleotide affinity modifications may allow for a greater number of mismatches compared to an unmodified compound. Similarly, certain oligonucleotide sequences may be more tolerant to mismatches than other oligonucleotide sequences. One of the skill in the art is capable of determining an appropriate number of mismatches between oligonucleotides, or between an oligonucleotide and a target nucleic acid, such as by determining melting temperature.

The antisense compounds herein, or a portion thereof, may have a defined percent identity to a sequence identification number (SEQ ID NO). As used herein, a sequence is identical to the sequence disclosed herein if it has the same nucleobase pairing ability, (e.g., a RNA which contains uracil in place of thymidine in the disclosed sequences of the instant invention would be considered identical as they both pair with adenine). This identity may be over the entire length of the oligomeric compound, or in a portion of the antisense compound. It is understood by those skilled in the art that an antisense compound need not have an identical sequence to those described herein to function similarly to the antisense compound described herein. Shortened versions of antisense compound taught herein, or non-identical versions of the antisense compound taught herein are contemplated within the various aspects and embodiments of the present invention. It is well known by those of ordinary skill in the art that it is possible to increase or decrease the length of an antisense compound and/or introduce mismatch bases without eliminating activity.

As described herein, oligomeric compounds of various aspects of the present invention—such as antisense oligonucleotides—may be targeted to certain nucleic acid molecules. And so, as used herein, "targeted to" refers to the process of designing an oligomeric compound such that the compound hybridizes with a selected nucleic acid molecule. "Targeting" an oligomeric compound to a particular target nucleic acid molecule can be a multistep process, which usually begins with the identification of a target nucleic acid whose expression is to be modulated. As used herein, the terms "target nucleic acid" and "nucleic acid encoding SMN2" encompass DNA encoding SMN2, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes SMN2. In one embodiment, the target nucleic acid is SMN2 pre-mRNA.

The targeting process may also include determination of at least one target region, segment, or site within the target nucleic acid for the antisense interaction to occur such that the desired effect (e.g., modulation of splicing) will result. "Region" is defined as a portion of the target nucleic acid having at least one identifiable structure, function, or characteristic. Target regions may include an exon or an intron. Within regions of target nucleic acids are segments, are defined as smaller or sub-portions of regions within a target nucleic acid. And sites are unique nucleobase positions within a target nucleic acid.

Still other aspects of the present invention include pharmaceutical compositions comprising one or more compounds described herein (e.g., oligomeric compounds, such as antisense oligonucleotides). And so the use of an antisense oligonucleotide for the preparation of a composition (e.g., medicament or therapeutic) for modulating splicing of an SMN2 pre-mRNA is also provided. In one aspect, such modulation of splicing results in an increase in exon 7 inclusion. Use of an antisense oligonucleotide provided herein for the preparation of a medicament for the treatment of spinal muscular atrophy is further provided.

The antisense compounds described herein and incorporated in pharmaceutical compositions by adding an effective amount of a compound to a suitable pharmaceutically acceptable diluent or carrier. Acceptable carriers and diluents are well known to those skilled in the art. Selection of a diluent or carrier is based on a number of factors, including, but not limited to, the solubility of the compound and the route of administration. Such considerations are understood by those of ordinary skill in the art. In one aspect, the antisense compounds of the present invention modulate splicing of SMN2. The compounds of the invention can also be used in the manufacture of a medicament for the treatment of diseases and disorders related to SMN2.

Another aspect of the present invention includes methods whereby bodily fluids, organs or tissues are contacted with an effective amount of one or more of the antisense compounds or compositions. Bodily fluids, organs or tissues can be contacted with one or more of the compounds of the invention resulting in modulation of SMN2 expression in the cells of bodily fluids, organs or tissues. An effective amount can be determined by monitoring the modulatory effect of the antisense compound or compounds or compositions on target nucleic acids or their products by methods routine to the skilled artisan. The pharmaceutical compositions of the present invention may be administered in a number of ways depending upon whether local or systemic treatment is desired and upon the area to be treated.

Such pharmaceuticals may have a therapeutic activity. Antisense compounds of the invention can be used to modulate the expression of SMN2 in an animal, such as a human. In one embodiment, the methods comprise the step of administering to a subject in need of therapy for a disease or condition associated with SMN2 an effective amount of an antisense compound that modulates expression of SMN2 (e.g. modulates splicing of SMN2). A disease or condition associated with SMN2 includes, but is not limited to, spinal muscular atrophy. In one embodiment, the antisense compounds of the present invention effectively modulate splicing of SMN2, resulting in an increase in exon 7 inclusion. Antisense compounds of the present invention that effectively modulate expression of SMN2 RNA or protein products of expression are considered active antisense compounds.

Modulation of expression of SMN2 can be measured in a bodily fluid, which may or may not contain cells; tissue; or organ of the animal. Methods of obtaining samples for analysis, such as body fluids (e.g., sputum, serum), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds of the invention, by routine clinical methods known in the art.

Thus, another aspect of the present invention includes the use of an isolated antisense compound targeted to SMN2 in the manufacture of a medicament for the treatment of a disease or disorder by means of the method described above. In one embodiment, the antisense compound is targeted to intron 6 of SMN2. In another embodiment, the antisense compound is targeted to intron 7 of SMN2. In yet another embodiment, the antisense compound is targeted to exon 7 of SMN2.

The antisense compounds described herein may comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds of the present invention, pharmaceutically acceptable salts of such prodrugs, and other bio equivalents. The term "prodrug" indicates a therapeutic agent that is prepared in an inactive or less active form that is converted to an active form (i.e., drug) within the body or cells thereof by the action of endogenous enzymes, chemicals, and/or conditions. The term "pharmaceutically acceptable salts" refers to physiologically and pharmaceutically acceptable salts of the compounds of the invention: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided. The antisense compounds of the invention may also be admixed, encapsulated, conjugated or otherwise associated with other molecules, molecule structures or mixtures of compounds.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

The compositions described herein can contain two or more antisense compounds. In another related embodiment, compositions can contain one or more antisense compounds, particularly oligonucleotides, targeted to a first nucleic acid and one or more additional antisense compounds targeted to a second nucleic acid target. Alternatively, compositions of the present invention can contain two or more antisense compounds targeted to different regions of the same nucleic acid target. Two or more combined compounds may be used together or sequentially. Compositions of the instant invention can also be combined with other non-antisense compound therapeutic agents.

And so, as described above, the use of oligomer compounds—such as the antisense oligonucleotides described herein—may be used to treat SMA in a subject, in that restoring SMN levels should have a beneficial impact on the SMA phenotype in a subject (e.g., a human). And so, increasing the amount of full-length SMN protein produced by the SMN2 gene by altering splicing is a promising therapeutic approach for treatment of SMA. The human SMN2/SMN1 gene contains numerous sequences that regulate the incorporation of SMN exon 7. FIG. 1 shows a schematic of a portion of the SMN2 gene. The SMN2 gene contains a series of elements that regulate the incorporation of exon 7. In particular, intron 6 and intron 7 contain negative regulatory sequences that in general bind hnRNP1 and encourage skipping of exon 7 [Bebee, T. W., Gladman, J. T. and Chandler, D. S. (2011) *Splicing regulation of the survival motor neuron genes and implications for treatment of spinal muscular atrophy*. Front Biosci, 15, 1191-1204]. These regulatory sequences can be blocked by an antisense oligonucleotide (ASO) thus encouraging the incorporation of SMN exon 7 in SMN2 [Hua, Y., Sahashi, K., Hung, G., Rigo, F., Passini, M. A., Bennett, C. F. and Krainer, A. R. (2010) *Antisense correction of SMN2 splicing in the CNS rescues necrosis in a type III SMA mouse model*. Genes Dev, 24, 1634-1644; Burghes, A. H. and McGovern, V. L. (2010) *Antisense oligonucleotides and spinal muscular atrophy: skipping along*. Genes Dev, 24, 1574-1579; Passini, M. A., Bu, J., Richards, A. M., Kinnecom, C., Sardi, S. P., Stanek, L. M., Hua, Y., Rigo, F., Matson, J., Hung, G. et al. (2011) *Antisense oligonucleotides delivered to the mouse CNS ameliorate symptoms of severe spinal muscular atrophy*. Sci Transl Med, 3, 72ra18]. To date the most effective antisense oligonucleotides (ASOs) have been directed to ISS-N1 in intron 7. However, numerous other regulatory elements have been reported in exon 6, intron 7, and exon 7 of SMN2. Aspects of the present invention identify alternatives to the ISS-N1 morpholino (MO). ISS-N2, identified by Singh, N. N., et al. (*An intronic structure enabled by a long-distance interaction serves as a novel target for splicing correction in spinal muscular atrophy*, Nucleic Acids Res 41, 8144-8165) has been shown to increase exon 7 incorporation in vitro.

In order to model SMA, mice have been developed containing a disrupted mouse Smn gene and the human SMN2 gene [see Monani, U. R., Sendtner, M., Coovert, D. D., Parsons, D. W., Andreassi, C., Le, T. T., Jablonka, S., Schrank, B., Rossol, W., Prior, T. W. et al. (2000) *The human centromeric survival motor neuron gene (SMN2) rescues embryonic lethality in Smn(−/−) mice and results in a mouse with spinal muscular atrophy*. Hum Mol Genet, 9, 333-339]. Mice possess only one Smn gene and the loss of this gene is embryonic lethal [Schrank, B. et al., *Inactivation of the survival motor neuron gene, a candidate gene for human spinal muscular atrophy, leads to massive cell death in early mouse embryos*, Proc. Natl Acad. Sci. USA 1997; 94:9920-9925]. Thus, the production of mice with an SMN deficiency that models human SMA required the introduction of the SMN2 gene. Two copies of human SMN2 in mice lacking Smn results in mice with severe SMA that live an average of 5 days, while eight copies of SMN2 results in complete rescue [Hsieh-Li, H. M., et al., *A mouse model for spinal muscular atrophy*. Nat. Genet. 2000; 24:66-70; Monari, U. R., et al., *The human centromeric survival motor neuron* gene (*SMN2*) rescues embryonic lethality in *Smn*(−/−) mice and results in a mouse with spinal muscular atrophy. Hum. Mol. Genet. 2000; 9:333-339]. The introduction of SMNΔ7, an SMN transgene lacking exon 7, into the severe SMA mice increases the average life span to ~14 days [Le, T. T., et al., *SMNDelta7, the major product of the centromeric survival motor neuron (SMN2) gene, extends survival in mice with spinal muscular atrophy and associates with full-length SMN*. Hum. Mol. Genet. 2005; 14:845-857]. It has recently been shown that postnatal induction of SMN can modulate SMA in SMN$^{\Delta 7}$ mice [Le, T. T., et al., *Temporal requirement for high SMN expression in SMA mice*. Hum. Mol. Genet. 2011; 20:3578-3591]. The SMNΔ7 mice can therefore serve as an SMA model that can be used to characterize disease-modifying pharmacologic interventions. This so called "delta7 SMA mouse" has become the most widely used mouse model of SMA [Le, T. T., Pham, L. T., Butchbach, M. E., Zhang, H. L., Monani, U. R., Coovert, D. D., Gavrilina, T. O., Xing, L., Bassell, G. J. and Burghes, A. H. (2005) *SMNDelta7, the major product of the centromeric survival motor neuron (SMN2) gene, extends survival in mice with spinal muscular atrophy and associates with full-length SMN*. Hum Mol Genet, 14, 845-857].

An increase in SMN, and rescue of the SMA phenotype, has been achieved with a single intracerebroventricular (ICV) injection of a morpholino ASO [Porensky, P. N., Mitrpant, C., McGovern, V. L., Bevan, A. K., Foust, K. D., Kaspar, B. K., Wilton, S. D. and Burghes, A. H. (2012) *A single administration of morpholino antisense oligomer rescues spinal muscular atrophy in mouse*. Hum Mol Genet, 21, 1625-1638]. In this regard, a single morpholino ASO administration resulted in an increase in survival from 14 days to over 100 days in delta7 SMA mice when delivered by ICV [Porensky, P. N., Mitrpant, C., McGovern, V. L., Bevan, A. K., Foust, K. D., Kaspar, B. K., Wilton, S. D. and Burghes, A. H. (2012) *A single administration of morpholino antisense oligomer rescues spinal muscular atrophy in mouse*. Hum Mol Genet, 21, 1625-1638]. This compares directly and favorably to MOE ASO administration, which gives an increase in survival to just 20-25 days [Passini, M. A., Bu, J., Richards, A. M., Kinnecom, C., Sardi, S. P., Stanek, L. M., Hua, Y., Rigo, F., Matson, J., Hung, G. et al. (2011) *Antisense oligonucleotides delivered to the mouse CNS ameliorate symptoms of severe spinal muscular atrophy*. Sci Transl Med, 3, 72ra18; Hua, Y., Sahashi, K., Rigo, F., Hung, G., Horev, G., Bennett, C. F. and Krainer, A. R. (2011) *Peripheral SMN restoration is essential for long-term rescue of a severe spinal muscular atrophy mouse model*. Nature, 478, 123-126].

Furthermore, the morpholino ASOs have shown no toxicity even at high doses whereas 8 μg/g of MOE ASO has demonstrated toxicity when given by ICV into neonatal mice [Passini, M. A., Bu, J., Richards, A. M., Kinnecom, C., Sardi, S. P., Stanek, L. M., Hua, Y., Rigo, F., Matson, J., Hung, G. et al. (2011) *Antisense oligonucleotides delivered to the mouse CNS ameliorate symptoms of severe spinal muscular atrophy*. Sci Transl Med, 3, 72ra18]. More specifically, an 18mer MOE chemistry ASO overlapping ISS-N1 effectively increases in vivo exon 7 incorporation and SMN levels through SMN2 splice modulation [Hua, Y., et al., *Antisense correction of SMN2 splicing in the CNS rescues necrosis in a type III SMA mouse model*. Genes Dev. 2010; 24:1634-1644; Hua, Y., et al., *Antisense masking of an hnRNP A1/A2 intronic splicing silencer corrects SMN2 splicing in transgenic mice*. Am. J. Hum. Genet. 2008; 82:834-848]. Intracerebroventricular (ICV) injection of this MOE at a dose of 0.58 mM did increase the average survival in SMNΔ7 SMA mice from 14 to 26 days [Passini, M. A., et al., *Antisense oligonucleotides delivered to the mouse CNS ameliorate symptoms of severe spinal muscular atrophy*. Sci. Transl. Med. 2011; 3:72ra18]. However, there was evidence of toxicity with this MOE at doses >1.16 mM. More recently, while this work was in review, Hua et al. [*Peripheral SMN restoration is essential for long-term rescue of a severe spinal muscular atrophy mouse model*. Nature 2011; 478:123-126] reported that peripheral dosing of MOEs was essential for longer survival, and propose that extra-CNS targets (i.e. peripheral) are required for rescue of the SMA phenotype. This assertion contradicts previous results showing the necessity of neuronal SMN expression using both scAAV8-SMN delivery by ICV, and transgenic approaches which limit SMN expression to CNS or peripheral tissue [Gavrilina, T. O., et al., *Neuronal SMN expression corrects spinal muscular atrophy in severe SMA mice while muscle-specific SMN expression has no phenotypic effect*. Hum. Mol. Genet. 2008; 17:1063-1075; Passini, M. A., et al., *CNS-targeted gene therapy improves survival and motor function in a mouse model of spinal muscular atrophy*. J. Clin. Invest. 2010; 120:1253-1264]; moreover, the authors show CNS SMN2 splicing modulation after serial high-dose peripheral deliveries, suggesting MOE transport across the blood-brain barrier when delivered at high doses in young mice.

Morpholinos, on the other hand, have a low toxicity and a wide distribution of uptake as evidenced by their extensive use in target gene expression knockdown in the developing zebrafish [Ellet, F., et al., *Zebrafish as a model for vertebrate hematopoiesis*. Curr. Opin. Pharmacol. 2010; 10:563-570]. MOs have been used to induce exon skipping in Duchenne muscular dystrophy (DMD) with excellent body-wide distribution and restoration of dystrophin expression after systemic administration in the mdx mouse [Alter, J., et al., *Systemic delivery of morpholino oligonucleotide restores dystrophin expression bodywide and improves dystrophic pathology*. Nat. Med. 2006; 12:175-177; Wu, B., et al., *One-year treatment of morpholino antisense oligomer improves skeletal and cardiac muscle functions in dystrophic mdx mice*. Mol. Ther. 2011; 19:576-583; Yokota, T. et al., *Efficacy of systemic morpholino exon-skipping in Duchenne dystrophy dogs*. Ann Neurol. 2009; 65:667-676]. Likewise, there have been encouraging clinical results in patients with DMD after MO administration [Kinali, M., et al., *Local restoration of dystrophin expression with the morpholino oligomer AVI-4658 in Duchenne muscular dystrophy: a single-blind, placebo-controlled, dose-escalation, proof-of-concept study*. Lancet Neurol 2009; 8:918-928; Cirak, S., et al., *Exon skipping and dystrophin restoration in patients with Duchenne muscular dystrophy after systemic phosphorodiamidate morpholino oligomer treatment: an open-label, phase 2, dose-escalation study*. Lancet 2011; 378:595-605; Sazani, P., et al., *Repeat-Dose Toxicology Evaluation in Cynomolgus Monkeys of AVI-4658, a Phosphorodiamidate Morpholino Oligomer (PMO) Drug for the Treatment of Duchenne Muscular Dystrophy*. Int. J. Toxicol. 2011; 30:313-321]. Thus many benefits could result from the development of an the ASO morpholino for treatment of SMA in humans.

Antisense oligomers (ASO), including 2'-O-methyl (2'-OMe) or 2'-O-methoxyethyl (MOE)-modified nucleotides on a phosphorothioate backbone, peptide nucleic acids (PNA) and phosphorodiamidate morpholino (MO) oligomers can be used as specific splice-switching agents to alter pre-mRNA processing [Baughan, T. D., et al., *Delivery of bifunctional RNAs that target an intronic repressor and*

*increase SMN levels in an animal model of spinal muscular atrophy.* Hum. Mol. Genet. 2009; 18:1600-1611; Wilton, S. D., et al., *Specific removal of the nonsense mutation from the mdx dystrophin mRNA using antisense oligonucleotides.* Neuromuscul. Disord. 1999; 9:330-338; Burghes, A. H., *Antisense oligonucleotides and spinal muscular atrophy: skipping along.* Genes Dev. 2010; 24:1574-1579]. ASOs can block targeted sequences, including exon splice enhancers or intron splice silencers (ISSs) [Wilton, S. D., et al., *Specific removal of the nonsense mutation from the mdx dystrophin mRNA using antisense oligonucleotides.* Neuromuscul. Disord. 1999; 9:330-338; Burghes, A. H., *Antisense oligonucleotides and spinal muscular atrophy: skipping along.* Genes Dev. 2010; 24:1574-1579; Williams, J. H., et al., *Oligonucleotide-mediated survival of motor neuron protein expression in CNS improves phenotype in a mouse model of spinal muscular atrophy.* J. Neurosci. 2009; 29:7633-7638; Alter, J., et al., *Systemic delivery of morpholino oligonucleotide restores dystrophin expression bodywide and improves dystrophic pathology.* Nat. Med. 2006; 12:175-177; Morcaos, P. A., *Achieving targeted and quantifiable alteration of mRNA splicing with morpholino oligos.* Biochem. Biophys. Res. Commun. 2007; 358:521-527]. Numerous regions are important in SMN2-splicing regulation [Bebee, T. W., et al., *Splicing regulation of the survival motor neuron genes and implications for treatment of spinal muscular atrophy.* Front Biosci. 2011; 15:1191-1204], and one particularly important element is the negative splice regulator ISS-N1, a 15 nucleotide-splice-silencing motif located downstream of SMN2 exon 7 [Singh, N. K., et al., *Splicing of a critical exon of human survival motor neuron is regulated by a unique silencer element located in the last intron.* Mol. Cell Biol. 2006; 26:1333-1346].

To that end, in a previous study [see Monani, U. R., Lorson, C. L., Parsons, D. W., Prior, T. W., Androphy, E. J., Burghes, A. H. and McPherson, J. D. (1999) *A single nucleotide difference that alters splicing patterns distinguishes the SMA gene SMN1 from the copy gene SMN2*, Hum Mol Genet, 8, 1177-1183], intron variations that occurred in milder than expected SMA patients were studied. The results indicate two regions that could be important in determining the severity of SMA and influence the splicing of SMN2. The first is the A/G at position –100 in intron 7 and the second region contains two variants located in intron 6. This conclusion was reached due to variants that occur between SMN1 and 2. The complete sequence of the SMN1 and SMN2 genes, including intronic sequence, is known. And there are very few variants between SMN1 and SMN2. That mentioned above is one of them and therefore a candidate to influence splicing of SMN2. Further, modulators of SMN2 splicing have been previously identified in intron 7, intron 6 and exon7 [see Kashima, T., Rao, N., and Manley, J. L. (2007). *An intronic element contributes to splicing repression in spinal muscular atrophy*, Proc Natl Acad Sci USA 104, 3426-3431].

And so, in certain aspects of the present invention, MO ASOs to these regions have been developed. Some ASOs are contiguous and some are designed to disrupt the secondary structure of the RNA thus they bind to non-contiguous areas of the intron. Below are provided the sequence of a number of embodiments of ASOs that have been designed in intron 7, intron 6 and exon 7 of SMN2. Each ASO may be shifted upstream or downstream by several nucleotides or may contain single or more nucleotide changes as we have shown that single base pair changes can increase the activity of the ASO. Further, each ASO that is bi-functional or tri-functional may contain linkers composed of "A"s in between the sets of contiguous base pairs. The sequences can be used for synthesis of morpholino ASO, 2MOE, BNA, LNA, Tricyclo oligonucleotide or any other ASO chemistry. The ASO may be administered to mouse models of SMA containing the human SMN2 gene. The method of administration may be injection. And when injected, the administration may occur via ICV, facial vein, IP or any other method of injection. The ASOs described herein are expected to increase SMN protein levels and full-length SMN transcript production in all tissues of the human SMN2 containing mouse models as measured by all standard methods including but not limited to western, ELISA, qPCR, ddPCR, etc.

ASOs Complementary to Intron 7 Sequences

As described above, a number of the oligomer compounds, in certain embodiments, are antisense oligonucleotides that are complementary to sequences located in intron 7 of SMN2. In eight specific embodiments, eight ASOs were developed, based on sequences located in SMN2 intron 7. The first and second sequences (of the eight sequences) complementary to portions of intron 7 (and the rationale for each) are:

```
ISS-N2(273, ΔA-297)25 mer-A
                                      [SEQ ID NO 1]
5'AAGTCTGCAGGTCTGCCTACTAGTG ISS-N2(273, ΔA, ΔA-297)25 mer-2A
                                      [SEQ ID NO 2]
5'AAGTCTGCAGGTCAGCCTACTAGTG
```

Figure 2:
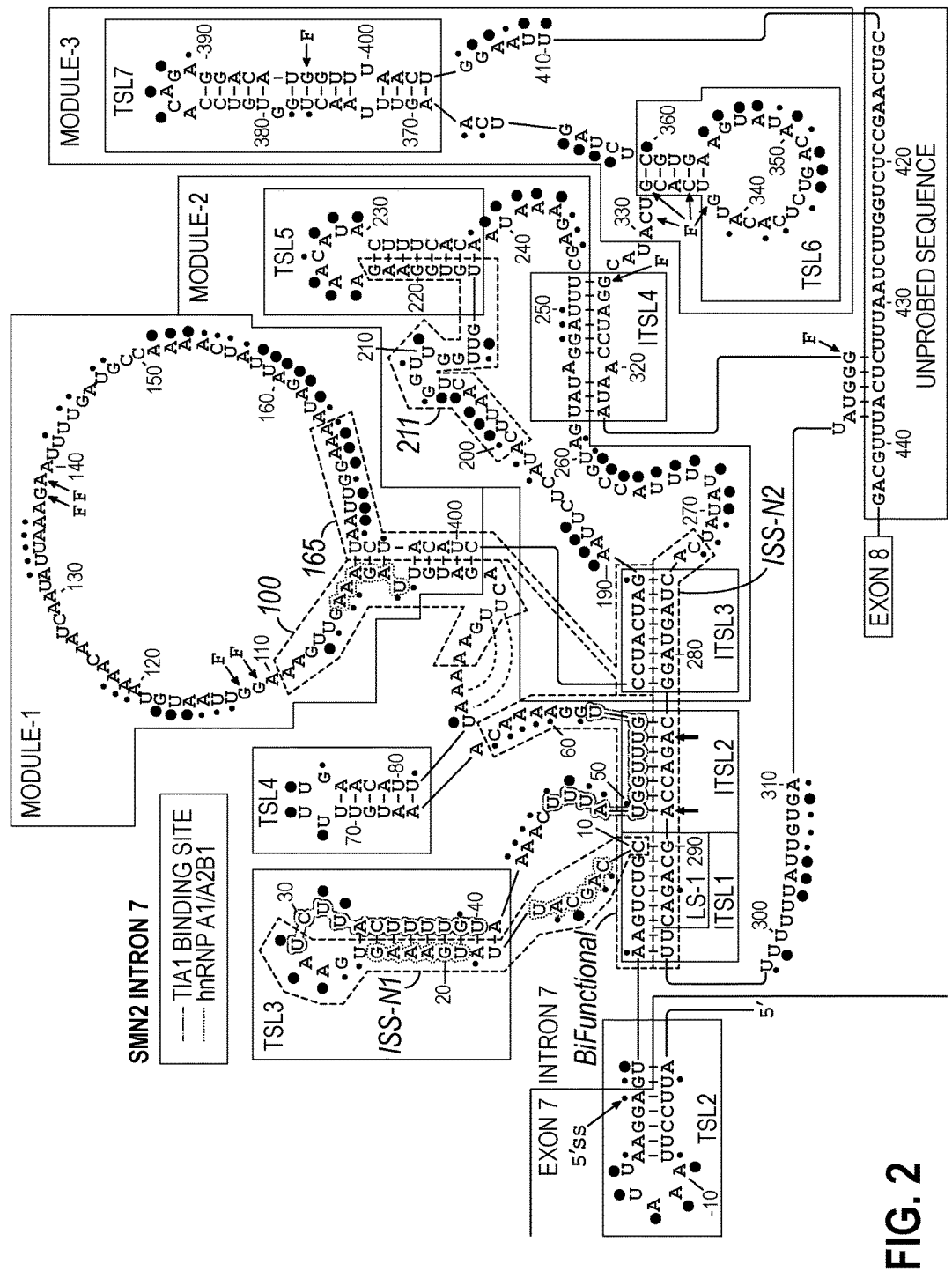
FIG. 2 is a schematic of the structure of SMN2 intron 7.

ISS-N2 is an ASO originally developed by Iowa State University (jointly owned with Sarepta Therapeutics, of Cambridge, Mass.). The above SEQ ID NOS 1 and 2 are ASOs that the present inventors have developed to contain some of ISS-N2 with either single nucleotide changes that increase activity of the ASO as measured by increased survival in the SMA mouse model compared to the original ISS-N2 sequence of AAGTCTGCTGGTCTGCCTAC [SEQ ID NO 3]. The first nucleotide of intron 7 is numbered 1, as shown in FIG. 2. FIG. 2 is a schematic of the structure of SMN2 intron 7 as predicted in Singh, N. N., Lawler, M. N., Ottesen, E. W., Upreti, D., Kaczynski, J. R. and Singh, R. N. (2013) *An intronic structure enabled by a long-distance interaction serves as a novel target for splicing correction in spinal muscular atrophy*, Nucleic Acids Res, 41, 8144-8165. The secondary structure of SMN2 intron 7 shown in FIG. 2, more specifically, is a SHAPE-derived structure of SMN2 intron 7. This structure is based on combined results produced with 10 extension primers (Supplementary Table S4). The large circles in FIG. 2 indicate nucleotides with normalized 1M7 reactivity >0.5, small circles indicate nucleotides with normalized 1M7 reactivity between 0.3 and 0.5. Locations of modules, ISTLs and TSLs have been indicated. Positions corresponding to RTase falloffs are marked with 'F'. Terminal Stem Loop 3 (TSL3), Module 1 and Module 2 are shown with some of the oligos highlighted in each. The star depicts the location of variant #96 and #97.

The third sequence (of the eight sequences) complementary to portions of intron 7 is:

```
in7(3 + 10, 50 + 64)BF
                                      [SEQ ID NO 4]
5'GTTTTCCACAAACCAGCAGACTT
```

This is an ASO developed by the present inventors that contains nucleotides (3-10) and (50-64) in SMN2 intron 7. These sequences were chosen because they are predicted to complex with part of the ISS-N2 sequence as part of the RNA secondary structure predicted in Singh, N. N., Lawler, M. N., Ottesen, E. W., Upreti, D., Kaczynski, J. R. and Singh, R. N. (2013) *An intronic structure enabled by a long-distance interaction serves as a novel target for splicing correction in spinal muscular atrophy*, Nucleic Acids Res, 41, 8144-8165. This ASO also increases activity of the ASO as measured by increased survival in the SMA mouse model compared to the original ISS-N2 sequence of AAGTCTGCTGGTCTGCCTAC [SEQ ID NO 3].

The fourth and fifth sequences (of the eight sequences) complementary to portions of intron 7 are:

```
Module 1 in7(85-109)
                                            [SEQ ID NO 5]
5'TTCAACTTTCTAACATCTGAACTTT Module 1 in7(165-189)
                                            [SEQ ID NO 6]
5'CTAGTAGGGATGTAGATTAACCTTT
```

These two ASOs disrupt the sequence around the A/G at −100 position nucleotide identified as a variant in milder than expected SMA patients; and this ASO also includes a G nucleotide at −96 that was identified in the original sequencing of the SMN2 gene [see Monani, U. R., Lorson, C. L., Parsons, D. W., Prior, T. W., Androphy, E. J., Burghes, A. H. and McPherson, J. D. (1999) *A single nucleotide difference that alters splicing patterns distinguishes the SMA gene SMN1 from the copy gene SMN2*, Hum Mol Genet, 8, 1177-1183] as a variant between SMN1 and SMN2.

The sixth sequence (of the eight sequences) complementary to portions of intron 7 is:

```
ISS-N2/module 1 in7(3-10, 50-56, 91-100)
                                            [SEQ ID NO 7]
5'CTAACATCTGCAAACCAGCAGACTT
```

This ASOs disrupts the sequence around the A/G at −100 position nucleotide identified as a variant in milder than expected SMA patients; and this ASO also includes a G nucleotide at −96 that was identified in the original sequencing of the SMN2 gene [see Monani, U. R., Lorson, C. L., Parsons, D. W., Prior, T. W., Androphy, E. J., Burghes, A. H. and McPherson, J. D. (1999) *A single nucleotide difference that alters splicing patterns distinguishes the SMA gene SMN1 from the copy gene SMN2*, Hum Mol Genet, 8, 1177-1183] as a variant between SMN1 and SMN2. The −100 area is a previously described hnRNPA1 binding site [as described in Kashima, T., Rao, N. and Manley, J. L. (2007) *An intronic element contributes to splicing repression in spinal muscular atrophy*, Proc Natl Acad Sci USA, 104, 3426-3431]. Nucleotides 3 to 10 of SMN2 intron 7 were chosen because they are predicted to complex with part of the ISS-N2 sequence as part of the RNA secondary structure predicted in Singh, N. N., Lawler, M. N., Ottesen, E. W., Upreti, D., Kaczynski, J. R. and Singh, R. N. (2013) *An intronic structure enabled by a long-distance interaction serves as a novel target for splicing correction in spinal muscular atrophy*, Nucleic Acids Res, 41, 8144-8165.

The seventh and eighth sequences (of the eight sequences) complementary to portions of intron 7 are:

```
module 2 in7(199-223)
                                            [SEQ ID NO 8]
5'CTTCCACACAACCAACCAGTTAAGT
```

```
ISS-N2/module2 in7(3-10)A(50-56)A(182-189)
                                            [SEQ ID NO 9]
5'CTAGTAGGTCAAACCATGCAGACTT
```

These ASOs disrupt module 2 as described in Singh, N. N., Lawler, M. N., Ottesen, E. W., Upreti, D., Kaczynski, J. R. and Singh, R. N. (2013) *An intronic structure enabled by a long-distance interaction serves as a novel target for splicing correction in spinal muscular atrophy*, Nucleic Acids Res, 41, 8144-8165. This ASO also includes a G nucleotide at −211 that was identified in the original sequencing of the SMN2 gene [see Monani, U. R., Lorson, C. L., Parsons, D. W., Prior, T. W., Androphy, E. J., Burghes, A. H. and McPherson, J. D. (1999) *A single nucleotide difference that alters splicing patterns distinguishes the SMA gene SMN1 from the copy gene SMN2*, Hum Mol Genet, 8, 1177-1183] a variant between SMN1 and SMN2. Nucleotides 3 to 10 and 50-56 of SMN2 intron 7 were chosen by the present inventors because these may complex with part of the ISS-N2 sequence as part of the RNA secondary structure predicted in Singh, N. N., Lawler, M. N., Ottesen, E. W., Upreti, D., Kaczynski, J. R. and Singh, R. N. (2013) *An intronic structure enabled by a long-distance interaction serves as a novel target for splicing correction in spinal muscular atrophy*, Nucleic Acids Res, 41, 8144-8165.

ASOs Complementary to Intron 6 Sequences

Further, as described above, a number of the oligomer compounds, in certain embodiments, are antisense oligonucleotides that are complementary to sequences located in intron 6 of SMN2. In specific embodiments, three ASOs were developed, based on sequences located in SMN2 intron 6. These sequences, complementary to portions of intron 6 (and the rationale for each) are:

```
in6 variant #96 in6(-378-352)
                                            [SEQ ID NO 10]
5'GCGTGGTGGCTCAGGCTAGGCACAG in6 variant #97 in6(-56-31)
                                            [SEQ ID NO 11]
5'TAGCTATATAGACATAGATAGCTAT in6 var#6, AA, #97(-360-371)AA(-49-38)
                                            [SEQ ID NO 12]
5'ATAGACATAGATTTGGCTCAGGCTA
```

These ASOs cover two nucleotide variants (#96 located at −367 and #97 located at −44, FIG. 2 starred) that were first described in Monani, U. R., Lorson, C. L., Parsons, D. W., Prior, T. W., Androphy, E. J., Burghes, A. H. and McPherson, J. D. (1999) *A single nucleotide difference that alters splicing patterns distinguishes the SMA gene SMN1 from the copy gene SMN2*, Hum Mol Genet, 8, 1177-1183, from the sequence of the SMN2 gene. More recently, it has been noted that both variants segregate together in SMA patients that are milder than expected. In other words, given the SMN2 copy number of the patient one would expect a more severe SMA phenotype than is found when both variants (#96 located at −367 and #97 located at −44) are present.

The last nucleotide of intron 6 is numbered −1

ASOs Complementary to Exon 7 Sequences

Further still, as described above, a number of the oligomer compounds, in certain embodiments, are antisense oligonucleotides that are complementary to sequences located in exon 7 of SMN2. This is due to the fact that exon 7 includes the originally defined sequence difference between SMN1 and SMN2, which is a modulator of splicing. In specific embodiments, five ASOs were developed, based on sequences located in SMN2 exon 7. These sequences, complementary to portions of exon 7 (and the rationale for each) are:

ex7(15-39)
[SEQ ID NO 13]
5'ATGTGAGCACCTTCCTTCTTTTTGA ex7(34-47)15 mer
[SEQ ID NO 14]
5'ATTTAAGGAATGTGA ex7(2-21)20 mer
[SEQ ID NO 15]
5'TTTTTGATTTTGTCTAAAAC ex7(9-21)A(34-45)
[SEQ ID NO 16]
5'AAGGAATGTGATTTTTTGATTTTGT ex7(5-18, 34-44)
[SEQ ID NO 17]
5'AAGGAATGTGATTGATTTTGTCTAA These sequences were determined in part from the work published by Hua, Y., Vickers, T. A., Baker, B. F., Bennett, C. F. and Krainer, A. R. (2007) *Enhancement of SMN2 exon 7 inclusion by antisense oligonucleotides targeting the exon*, PLoS Biol, 5, e73. In that study, a microwalk was performed in exon 7 and mini gene expression in HEK293 cells was used to determine SMN exon 7 incorporation. Sequences were chosen by including nucleotides that enhanced incorporation of SMN exon 7 and excluding nucleotides that inhibited SMN exon 7 incorporation in that study. The first nucleotide of exon 7 is numbered 1. And so, data from the microwalks performed by Hua et al was studied by the present inventors in order for the present inventors to determine what sequences would be included or excluded when designing the present morpholino ASOs complementary to exon 7. Prior to this, no 25mer MO ASOs had been prepared and ICV injected into mice for increased full length SMN (FL-SMN) and survival.

The various aspects of the present invention will be described in greater detail with respect to the following nonlimiting Examples. Further, while certain compounds, compositions and methods related to the present invention have been described with specificity in accordance with certain embodiments, the following Examples serve only to illustrate compounds of the invention and are not intended to limit the same. Further, the references, GenBank accession numbers, and the like recited in the present application are incorporated by reference herein in their entireties.

Example

This Example generally describes experiments performed to test the ability of the MO ASOs described above to increase full-length SMN (FL-SMN) and survivability in SMA subjects. In doing so, MO ASOs were designed and synthesized, and SMA mice generated and genotyped. ASOs were then administered to mice, and survival and FL-SMN of the mice was analyzed.

Materials and Methods
Morpholino Antisense Oligomers
Materials used in this Example include certain of the sixteen morpholino antisense oligomers complementary to regions in intron 7, intron 6, or exon 7, as described above. More specifically, nine of those sixteen ASOs were used (7 complementary to intron 7, 1 complementary to intron 6, and one complementary to exon 7). Those are shown in Table 1 (below).

TABLE 1

Nine novel Morpholino ASO sequences and their location in the SMN2 gene.

| Common Name | Name on Label | Antisense Sequence |
|---|---|---|
|  | ISS-N2-25 mer-A | AAGTCTGCAGGTCTGCCTAC TAGTG [SEQ ID NO 1] |
|  | ISS-N2-25 mer-2A | AAGTCTGCAGGTCAGCCTAC TAGTG [SEQ ID NO 2] |
|  | (-3-10)(-50-64)BF | GTTTTCCACAAACCAGCAGA CTT [SEQ ID NO 4] |
| -100 | in7(85-109) | TTCAACTTTCTAACATCTGA ACTTT [SEQ ID NO 5] |
| -165 | in7(165-189) | CTAGTAGGGATGTAGATTAA CCTTT [SEQ ID NO 6] |
|  | in7(3-10, 50-56, 91-100) | CTAACATCTGCAAACCAGCA GACTT [SEQ ID NO 7] |
|  | in7(199-223) | CTTCCACACAACCAACCAGT TAAGT [SEQ ID NO 8] |
|  | ex7(2-21) | TTTTTGATTTTGTCTAAAAC [SEQ ID NO 15] |
| Intron 6 variant #96 & #97 | in6(361-371) (48-37) | ATAGACATAGATTTGGCTCA GGCTA [SEQ ID NO 12] |

Materials used in this Example also include three morpholino antisense oligomers complementary to regions in intron 7 already published by L. Price and S. Wilton. Those are shown in Table 2 (below).

TABLE 2

Morpholino antisense oligomers complementary to regions in intro 7, and their location in the SMN2 gene.

| Common Name | Name on Label | Antisense Sequence |
|---|---|---|
| -80 | in7(80-104) | CTTTCTAACATCTGAACTTTTAAA [SEQ ID NO 18] |
| -88 | in7(88-112) | CCTTTCAACTTTCTAACATCTGAAC [SEQ ID NO 19] |
| -93 | in7(93-117) | ATTAACCTTTCAACTTTCTAACATC [SEQ ID NO 20] |

Preparation of Morpholino Antisense Oligomers
Oligomer Synthesis: As is known to those of ordinary skill in the art, oligomerization of modified and unmodified nucleosides can be routinely performed according to literature procedures for DNA (e.g., Protocols for Oligonucleotides and Analogs, Ed. Agrawal (1993), Humana Press) and/or RNA (e.g., Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Further, antisense compounds to be used in various aspects of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

The twelve antisense oligonucleotides described in this Example (and shown in Tables 1 and 2, above) were synthesized by Gene Tools LLC of Philomath, Oreg.

Oligomer Purification and Analysis: Methods of oligonucleotide purification and analysis are known to those skilled in the art. Analysis methods include capillary electrophoresis (CE) and electrospray-mass spectroscopy. Such synthesis and analysis methods can be performed in multi-well plates. Any methods related to the various aspects of the present invention are not limited by the method of oligomer purification.

Generation of SMA Mice

As described above, mice were made by the inventors of the present application. More specifically, $SMN^{\Delta 7}$ carrier breeding mice (SMN2+/+; Smn+/−; SMNΔ7+/+) were crossed to generate three types of offspring varying in mouse Smn genotype: Smn+/+, Smn+/− and Smn−/− [using methods as described previously in Le, T. T., Pham, L. T., Butchbach, M. E., Zhang, H. L., Monani, U. R., Coovert, D. D., Gavrilina, T. O., Xing, L., Bassell, G. J. and Burghes, A. H. (2005) *SMNDelta7, the major product of the centromeric survival motor neuron (SMN2) gene, extends survival in mice with spinal muscular atrophy and associates with full-length SMN*. Hum Mol Genet, 14, 845-857 and Monani, U. R., Sendtner, M., Coovert, D. D., Parsons, D. W., Andreassi, C., Le, T. T., Jablonka, S., Schrank, B., Rossoll, W., Prior, T. W., et al. (2000). The human centromeric survival motor neuron gene (SMN2) rescues embryonic lethality in Smn(−/−) mice and results in a mouse with spinal muscular atrophy. Hum Mol Genet 9, 333-339, the disclosures of which are incorporated by reference herein in their entireties]. All breeding and subsequent use of animals in this study were approved by the IACUC of The Ohio State University, Columbus, Ohio, USA.

Mouse Genotyping

The SMN2, Smn knockout allele and SMNΔ7 alleles were genotyped as described previously [in Le, T. T., Pham, L. T., Butchbach, M. E., Zhang, H. L., Monani, U. R., Coovert, D. D., Gavrilina, T. O., Xing, L., Bassell, G. J. and Burghes, A. H. (2005) *SMNDelta7, the major product of the centromeric survival motor neuron (SMN2) gene, extends survival in mice with spinal muscular atrophy and associates with full-length SMN*. Hum Mol Genet, 14, 845-857; Monani, U. R., Sendtner, M., Coovert, D. D., Parsons, D. W., Andreassi, C., Le, T. T., Jablonka, S., Schrank, B., Rossoll, W., Prior, T. W., et al. (2000). *The human centromeric survival motor neuron gene (SMN2) rescues embryonic lethality in Smn(−/−) mice and results in a mouse with spinal muscular atrophy*, Hum Mol Genet 9, 333-339; and Porensky, P. N., Mitrpant, C., McGovern, V. L., Bevan, A. K., Foust, K. D., Kaspar, B. K., Wilton, S. D., and Burghes, A. H. (2012), *A single administration of morpholino antisense oligomer rescues spinal muscular atrophy in mouse*, Hum Mol Genet 21, 1625-16381. Tail snips were gathered at P0, and each pup was identified by paw tattooing. All genotyping was performed on P0 as described in the citations listed in this paragraph.

ICV Injections

A P0 or P4 pup was cryo-anesthetized and hand-mounted over a back-light to visualize the intersection of the coronal and sagittal cranial sutures (bregma) (55,58). A fine-drawn capillary needle with injection assembly was inserted 1 mm lateral and 1 mm posterior to bregma, and then tunneled 1 mm deep to the skin edge (approximating) ipsilateral lateral ventricle. An opaque tracer (Evans Blue, 0.04%) was added to the reagent to visualize the borders of the lateral ventricle after injection of 2-4 µl of MO.

Procedure for Dosing Mice: All studies will be carried out using SMA affected mice which are generated by crossing the carrier parents which are heterozygous for the mouse knockout allele and homozygous for all other transgenes (SMN2+/+, SMNΔ7+/+, Smn+/−). At PND1 (here defined as date of birth, equivalent to P0) pups will be tattooed and genotyped with a rapid genotyping protocol. Briefly mothers are temporally moved to separate housing. The appropriate dose of morpholino will be mixed with isotonic saline and Iohexol in a siliconized microfuge tube. The cryo-athesthetized pup will be hand-mounted over a back-light. A fine-drawn capillary needle with an injection assembly is inserted 1 mm lateral and 1 mm posterior to bregma and then tunneled 1 mm deep to the skin edge (approximately) into the ipsilateral lateral ventricle. An opaque tracer (Evans blue 0.04%) can be added to the reagent to visualize the borders of the lateral ventricle after injection. The volume of injection will be 2 µl and will not exceed 4 µl. Animals that do not receive proper injections will be excluded from analysis. A scrambled oligonucleotide and equivalent concentration will be used as control. All liters are culled to at most 5 animals to keep a consistent size of litter for feeding. The injector and evaluator are blinded to genotype of the animals and the randomization of litters is performed independently.

As described above, the antisense oligonucleotides described in this Example (and shown in Tables 1 and 2, above) were synthesized at Gene Tools LLC of Philomath, Oreg. In general, the MO ASOs were resuspended in sterile 0.9% sodium chloride, aliquoted and mixed with Evans Blue (final concentration 0.04%). Three different molar concentrations were prepared (high: 6 mM=40.5 µg/µl; middle: 4 mM=27 µg/µl; low: 2 mM=13.5 µg/µl). Stock solutions were stored at −20° C., and working solutions were stored at 4° C. Two microliters of MO oligomer (2 µl) were injected, yielding total doses per animal of 81 µg (high), 54 µg (middle) and 27 µg (low). The dose amounts described here are originally the same dosages as used previously in Porensky, P. N., Mitrpant, C., McGovern, V. L., Bevan, A. K., Foust, K. D., Kaspar, B. K., Wilton, S. D., and Burghes, A. H. (2012), *A single administration of morpholino antisense oligomer rescues spinal muscular atrophy in mouse*, Hum Mol Genet 21, 1625-1638, and are applicable to use with ISS-N1. In the present Example, however, as high as 10 mM stock solutions were used, and at times triple injections were performed with as high a dose total as 332 µg. The µg concentration delivered will depend on, and can be calculated from, the molecular weight.

Figure 3:
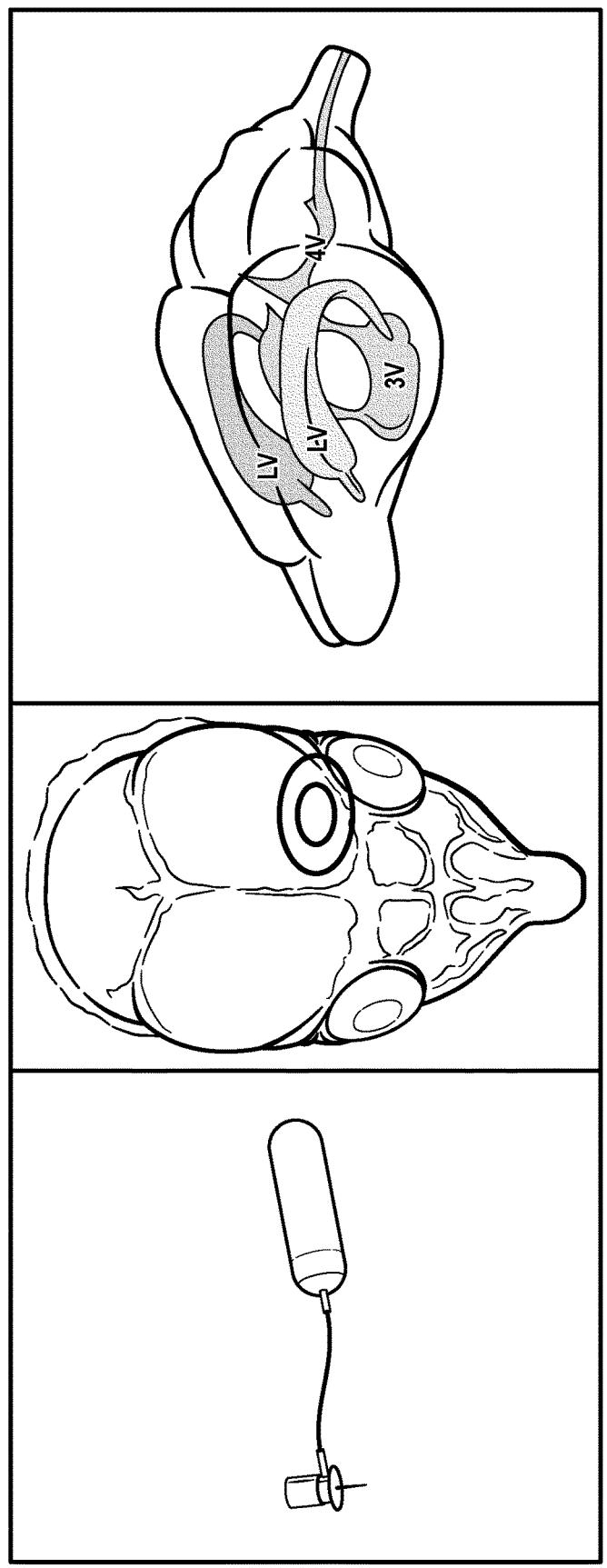
FIG. 3 includes a drawing of osmotic pump which may be used for injection of ASO into mice, and a photograph and drawing view of the brain of a mouse.

Re-administration of morpholino: Apart from injections, an osmotic pump has been used to test re-administration of ISS-N1 (it is planned that this pump will also be used to test readministration of the ASOs of aspects of the present invention described herein, but this has not yet been done). FIG. 3 includes an image of Alzet osmotic pump Model 1004. 27 µg of ISS-N1 was first injected on P0 by ICV and then re-administered at 30 days via an Alzet osmotic pump placed directly into the ventricle. The ISS-N1 MO diffused continuously at a rate of 1.4 µg/day for 30 days into the CSF until the contents of the pump were exhausted. The total amount of MO administered was 48 µg.

The following is a procedure developed for the future use of the pump with ASOs, and is the procedure followed when using the pump for readministration of ISS-N1: PND30 mice will be anesthetized with inhalational isoflurane (mixed with high flow 100% O2) at 3-5% for induction and 2-5% for maintenance. The animal is placed in a cranial stereotactic frame with digital coordinate guidance and the anesthesia nose cone secured. The mouse is secured to the stereotactic system with bilateral pins entering the external auricular canal, as well as with a rostral nose cone. The cranial midline is shaved from bregma to lambda, and the skin is prepared with betadine. The skin is incised and periosteum elevated to reveal suture lines. The cranium is leveled to ensure that bregma and lambda lay within the same axial plane. The stereotactic system, with attached nanoinjector and cranial probe, is zeroed over bregma. Intraventricular delivery is achieved by delivery to a set of predetermined coordinates in the x/y/z axes with respect to bregma [as described in Paxinos, G., Franklin, K. B. J. and Franklin, K. B. J. (2013) Paxinos and Franklin's the mouse brain in stereotaxic coordinates. Boston: Elsevier/Academic Press, Amsterdam]. A craniotomy is created with a high-speed burr over the aforementioned entry point, and the stereotactic probe is then inserted into the ipsilateral lateral ventricle. After cannulation of the cerebral ventricle, the implanted cannula will be connected to a tunneled catheter leading to the subcutaneous osmotic pump implanted in the dorsal intrascapular area of the mouse. A subcutaneous pocket will be created adjacent to but not underneath the skin incision to ensure proper wound healing and avoidance of wound breakdown. Surgical preparation of the intrascapular site is identical to the cranial prep. The incision will be closed with interrupted full thickness absorbable suture. The flow rate can be variable depending on predetermined settings we will use 0.11 µl/hr (4 week maximum) and the total dose for a starting dose of 18 ug/g will be (18 ug/g+44.8 ug/g). For each of the starting doses the concentration of the MO in the osmotic pump will be adjusted. Thus a lower concentration is used for the lower initial dose. The complete amount of MO delivered over time will be recorded. The survival of the animals per complete dose of MO will be determined. The MO will be mixed with Iohexol which we have found increases distribution of the MO throughout the CNS and results in alteration of SMN2 at all levels of the spinal cord.

Survival and FL-SMN Analysis

All injected animals were monitored each day for mortality. Further, all injected animals were assayed for full-length SMN (FL-SMN) via droplet digital PCR.

Droplet Digital PCR cDNA was collected via methods that are known to those of ordinary skill in the art. Primers and probe used for ddPCR were as follows: The SMNΔ7 transgene lacks the terminal portion of exon 8. Primers were designed to amplify only the SMN2 transcripts that contain this region, thus distinguishing SMNΔ7 from SMN2:

```
                                      [SEQ ID NO 21]
(hSMN2E8rev) TTATATACTTTTAAACATATAGAAGATAG,

[SEQ ID NO 22]
(hSMNE6fwd) AGATTCTCTTGATGATGCTGAATG.
```

PCR products were assayed for full-length SMN2 transcripts relative to cyclophilin. SMN2 amplification: (hSM-NFull Fb) GTTTCAGACAAAATCAAAAAGAAGGA [SEQ ID NO 23], (hSMNFull Rc) TCTATAACGCTTCA-CATTCCAGATCT [SEQ ID NO 24], probe: (hSMNFull FAM) ATGCCAGCATTTCTCCTTAATTTAAGG [SEQ ID NO 25]. Cyclophilin: (QcycloF) GTCAACCCCACCGT-GTTCTT [SEQ ID NO 26], (QcycloR) TTGGAACTTT-GTCTGCAAACA [SEQ ID NO 27], probe: (Probecyclo VIC) CTTGGGCCGCGTCT [SEQ ID NO 28]. PCR for SMN2 used 2 µl of cDNA and 0.6 µl (300 nm) of forward and reverse primers; cyclophilin, 1.8 µl (900 nM) forward and reverse primer.

PCR for SMN2 used 1.0 µl of cDNA and 0.1 µl of cyclophilin. 1.8 µl (900 nm) of forward and reverse primers was used for both SMN2 and cyclophilin. Droplet generation and reader analysis were performed on QuantaLife (www.quantalife.com/, now Bio-Rad) hardware. Ten to fifteen thousand droplets containing cDNA transcript and PCR reagents were generated before amplification. The concentration of transcripts was first calculated by the droplet reader using Poisson statistical distributions (65), and relative SMN2 levels were determined by calculating the ratio of SMN2 versus cyclophilin.

Results

The results of the procedures of this Example (i.e., data regarding the survival of the tested mice, and which mice exhibited FL-SMN) is shown largely in FIGS. 4-9 of the present application, as well as in Table 3 (below).

Figure 4:
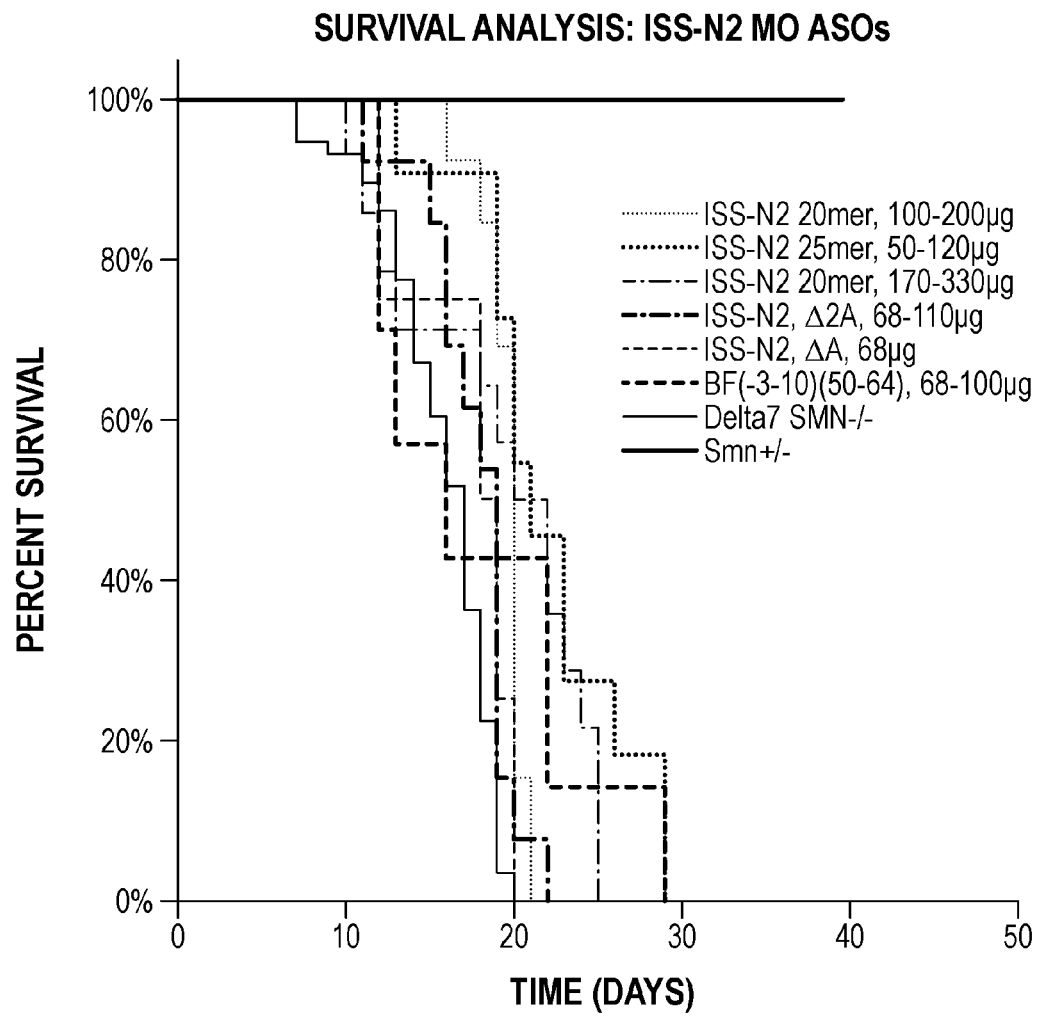
FIG. 4 is a graph depicting a survival analysis of ISS-N2 variants when administered to delta 7 SMA mice at P0 by ICV.
Figure 5:
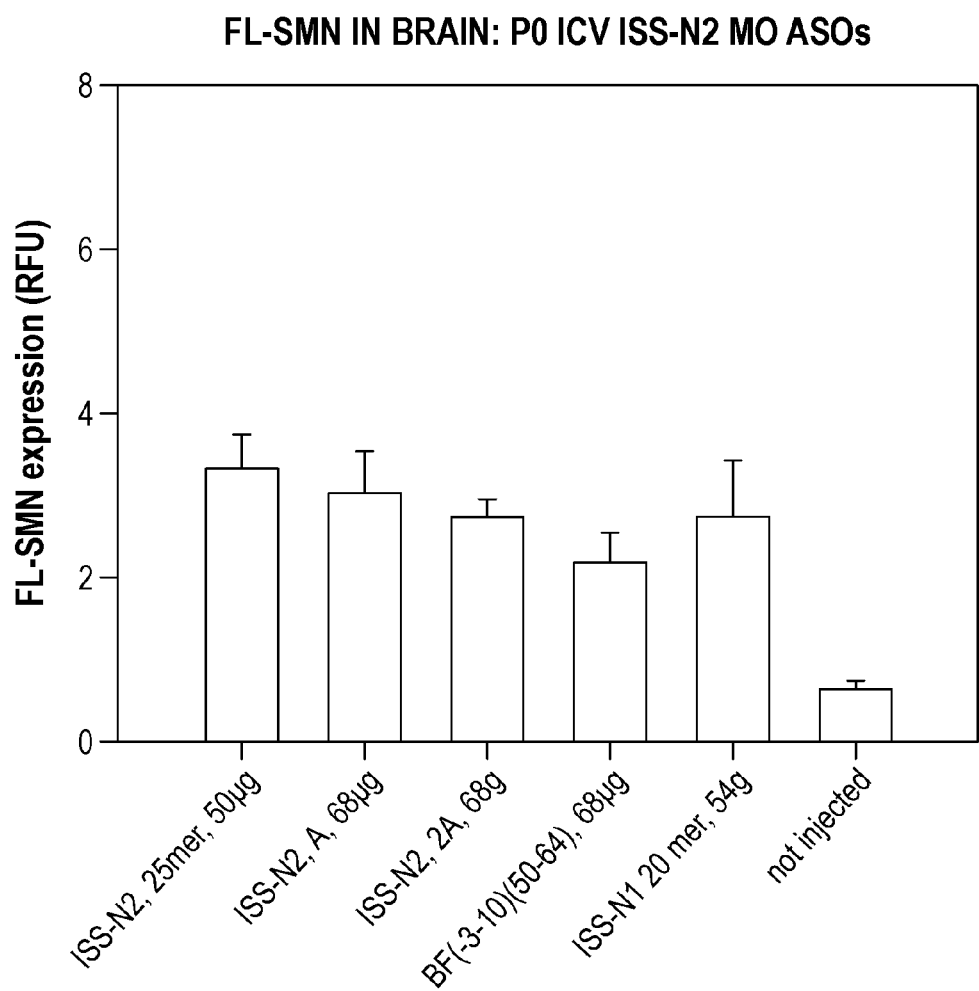
FIG. 5 is a graph comparing full-length SMN expression was measured at P7 in the brain of Delta7 mice after a single P0 ICV administration of various ISS-N2 morpholino antisense oligonucleotides (MO ASOs).

FIG. 4 is a graph depicting a survival analysis of ISS-N2 variants when administered to delta 7 SMA mice at P0 by ICV. And FIG. 5 is a graph comparing full-length SMN expression was measured at P7 in the brain of Delta7 mice after a single P0 ICV administration of various ISS-N2 MO ASOs. Quantitative droplet digital PCR (as described above) was performed on 3 biological replicates for each concentration.

Figure 6:
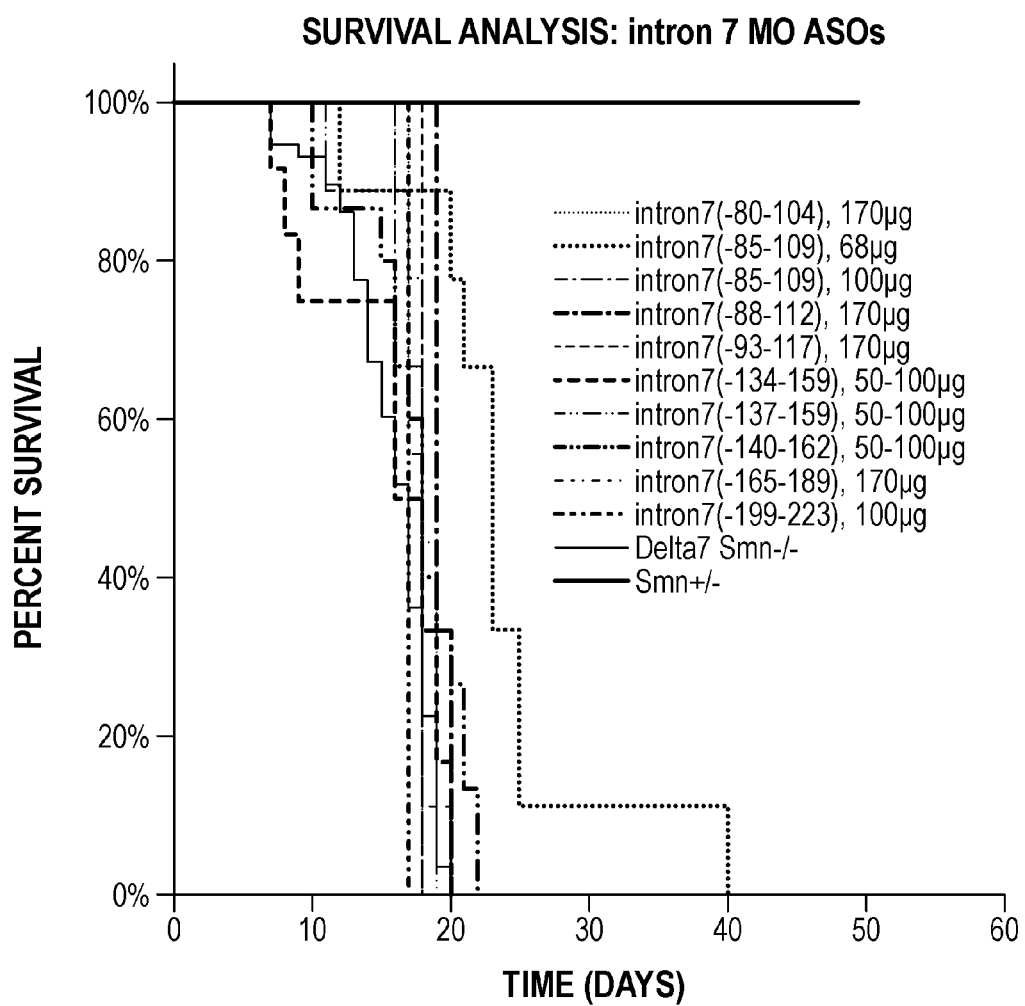
FIG. 6 is a graph depicting a survival analysis of novel SMN2 intron 7 MO ASOs when administered to delta7 SMA mice at P0 by ICV.
Figure 7:
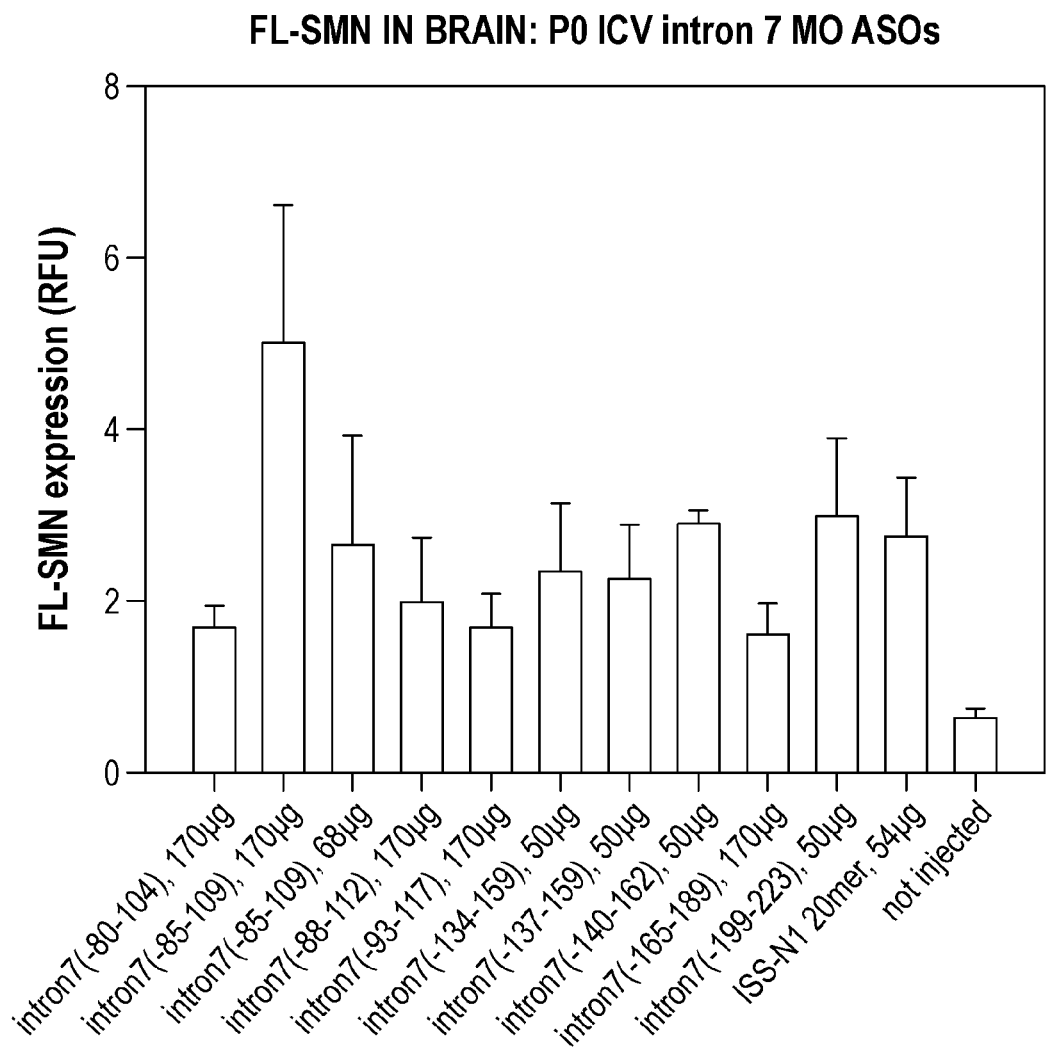
FIG. 7 is a graph comparing full-length SMN expression was measured at P7 in the brain of Delta7 mice after a single P0 ICV administration of intron 7 MO ASOs.

FIG. 6 is a graph depicting a survival analysis of novel SMN2 intron 7 MO ASOs when administered to delta7 SMA mice at P0 by ICV. And FIG. 7 is a graph comparing full-length SMN expression was measured at P7 in the brain of Delta7 mice after a single P0 ICV administration of intron 7 MO ASOs. Quantitative droplet digital PCR (as described above) was performed on 3 biological replicates for each concentration.

Table 3 (below) is a summary of survival data from administration of MO ASOs by ICV in delta7 P0 mice.

TABLE 3

Summary of survival data from administration of MO ASOs by ICV in delta7 P0 mice.

| ASO | Dose (µg) | Survival mean (days) | Survival max (days) | n |
|---|---|---|---|---|
| ISS-N2 20mer | ~200 | 18 | 29 | 7 |
| ISS-N2 25mer | 50-120 | 19 | 25 | 14 |
| ISS-N2 25mer | 170-330 | 22 | 29 | 11 |
| ISS-N2 ΔA | 68 | 17 | 20 | 4 |
| ISS-N2 Δ2A | 68-110 | 20 | 21 | 6 |
| in7(-3-10)(-50-64) | 68-100 | 18 | 22 | 13 |
| In7(80-104) | 170 | 17 | 18 | 3 |
| In7(85-109) | 68 | 24 | 40 | 9 |
| In7(85-109) | 100 | 17 | 18 | 2 |
| In7(88-112) | 170 | 19 | 20 | 3 |
| In7(93-117) | 170 | 18 | 18 | 2 |
| In7(134-159) | 50-100 | 18 | 19 | 9 |
| In7(137-159) | 50-100 | 16 | 20 | 12 |
| In7(140-162) | 50-100 | 18 | 22 | 15 |
| In7(165-189) | 170 | 18 | 20 | 9 |

TABLE 3-continued

Summary of survival data from administration of MO ASOs by ICV in delta7 P0 mice.

| ASO | Dose (μg) | Survival mean (days) | Survival max (days) | n |
|---|---|---|---|---|
| In7(199-223) | 100 | 17 | 17 | 2 |
| ISS-N1 | 54 | 104 | 119 | 10 |
| ISS-N1 | 27 | 83 | 120 | 8 |
| ISS-N1 | P0: 27 P30-P60: 1.4 μg/day = 48 | 180 | 192 | 2 |
| Δ7 SMA scramble | 50 | 15 | 19 | 8 |
| Δ7 SMA no injection | 0 | 15 | 20 | 58 |

Figure 8:
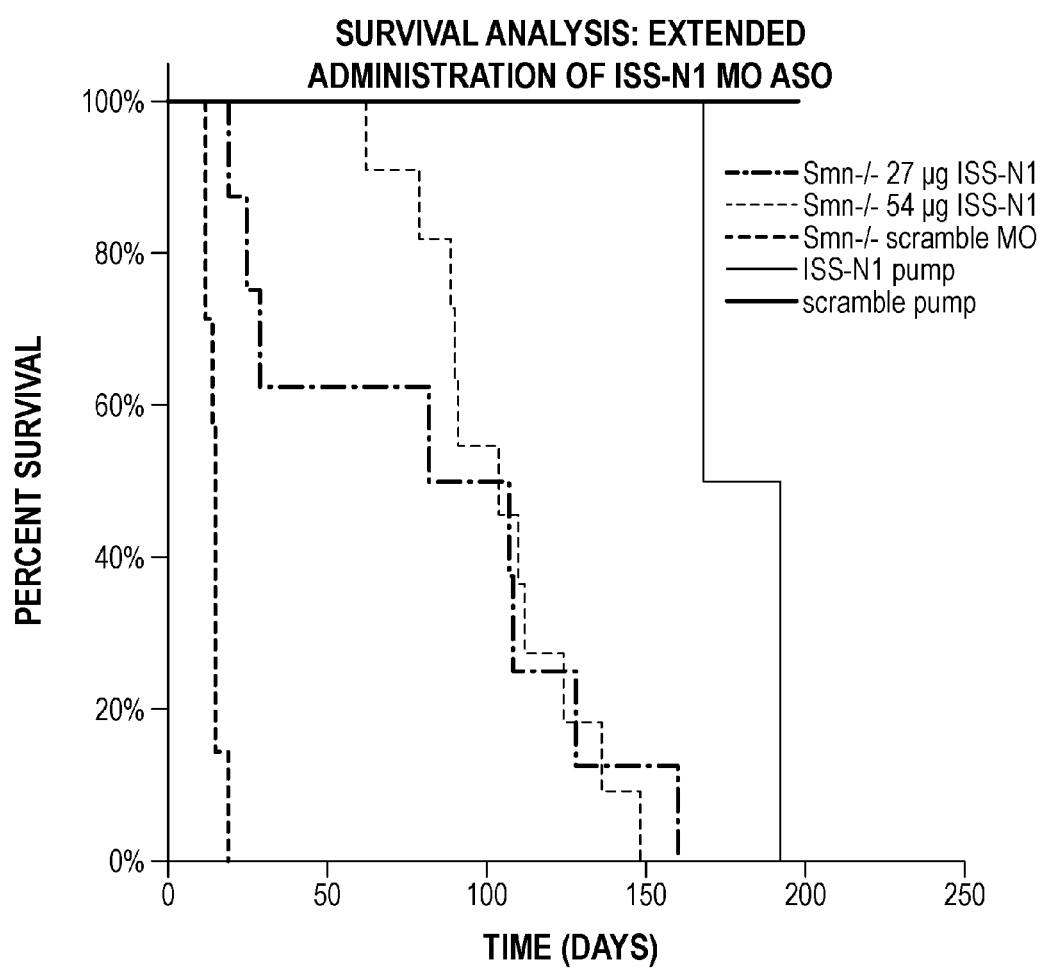
FIG. 8 is a graph depicting a survival analysis of delta 7 SMA mice upon ICV and continuous administration of ISS-N1 MO ASO via osmotic pump.
Figure 9:
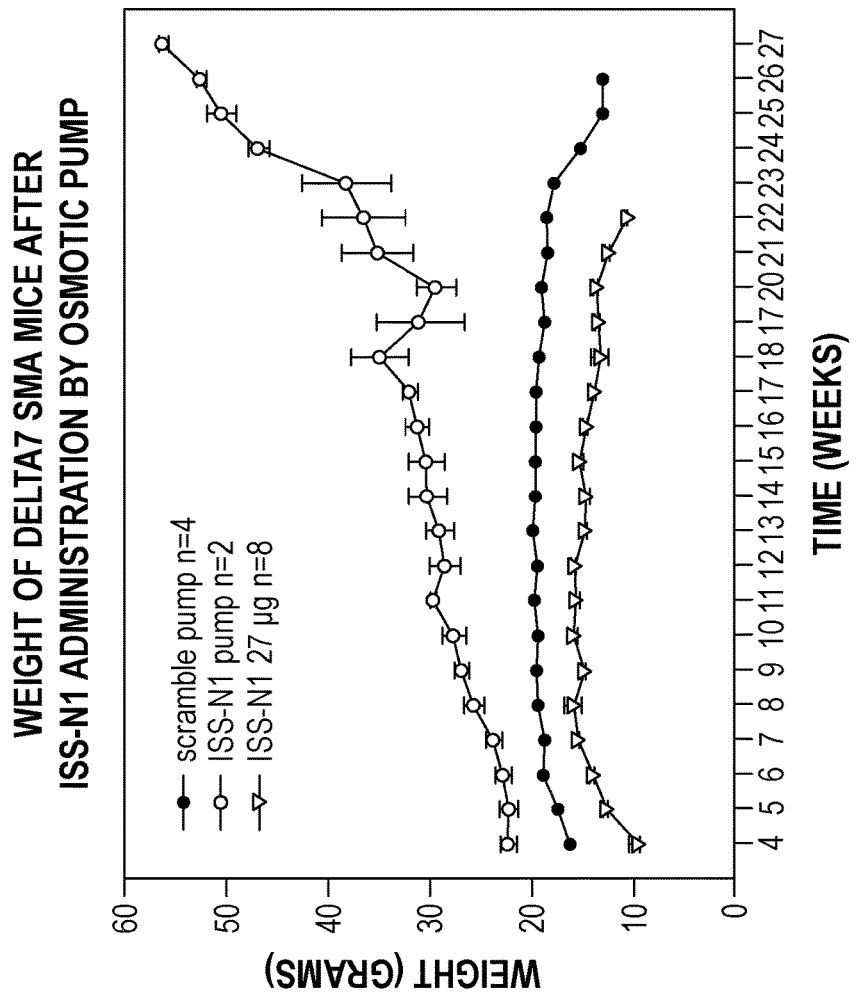
FIG. 9 is a graph depicting a weight analysis of delta 7 SMA mice upon ICV and continuous administration of ISS-N1 MO ASO via osmotic pump.

FIG. 8 is a graph depicting a survival analysis of delta 7 SMA mice upon ICV and continuous administration of ISS-N1 MO ASO via Osmotic Pump. Continuous delivery resulted in an average 100-day increase in survival over the single injection (n=2, 192 days and 168 day survival vs. single P1 27 μg ISS-N1 MO injection, n=8, mean 83 days or 12 weeks). Ear and tail necrosis was delayed by approximately 30 days (P88 vs. P55 in P0 single ICV injected control with no pump.) At day 60 the pump should be exhausted yet necrosis was not observed for another month. And FIG. 9 is a graph depicting a weight analysis of delta 7 SMA mice upon ICV and continuous administration of ISS-N1 MO ASO via Osmotic Pump. Continuous delivery resulted in an average 20% increase in weight over the single injection (n=2, max 19 g vs. single P1 27 μg ISS-N1 MO injection, n=8, max 14 g). The increase in weight was more pronounced by 20 weeks of age.

Discussion

SMA therapy is dependent on inducing SMN to sufficient levels in the correct cell type. As described herein, morpholino based antisense oligonucleotides have been developed that induce full-length SMN (FL-SMN). Indeed both ISS-N2 (Iowa State/Sarepta Therapeutics) and In7(85-109) reported here show either equivalent or even greater induction of FL-SMN than ISS-N1. However their impact on survival is less than ISS-N1 when ISS-N1 is dosed as a morpholino [see Porensky, P. N., Mitrpant, C., McGovern, V. L., Bevan, A. K., Foust, K. D., Kaspar, B. K., Wilton, S. D. and Burghes, A. H. (2012) *A single administration of morpholino antisense oligomer rescues spinal muscular atrophy in mouse*, Hum Mol Genet, 21, 1625-1638]. In particular P0 ICV administration of intron7(−85-109) at 68 μg increases SMN exon 7 incorporation and increases survival in the delta7 SMA mouse (P=0.00011 vs. Delta7 SMA). These mice have lived up to 40 days. This is comparable or better than prior developed MOE backbone antisense oligonucleotides when given by the same route (ICV) [Passini, M. A., Bu, J., Richards, A. M., Kinnecom, C., Sardi, S. P., Stanek, L. M., Hua, Y., Rigo, F., Matson, J., Hung, G. et al. (2011) *Antisense oligonucleotides delivered to the mouse CNS ameliorate symptoms of severe spinal muscular atrophy*, Sci Transl Med, 3, 72ra18]. Morpholinos (MO), as described above, can be used at very high concentrations. We used ~330 μg in the current studies by ICV administration and showed no toxicity in the mouse.

One conclusion from these studies is that amount of FL-SMN induction in brain tissue does not correlate to a proportional increase in survival in mice. This can be seen for a morpholino against ISS-N1 and intron7 (85-109). The same level of SMN induction is achieved but not the same increase in survival. It is thus important to consider why this occurs and how it can be changed. It is believed that the most likely reason for this difference, at least with morpholino based ASOs, is that the uptake by specific cell types is sequence specific. In turn, some critical cell types do not take up the intron7(−85-109) sequence efficiently. Uptake by tissues can be changed by a number of means. Including attachment of specific peptides can lower the dose of morpholino ASO required for efficacy as well as expand the tissues and cell types that can be transduced [Järver, P., Coursindel, T., Andaloussi, S. E., Godfrey, C., Wood, M. J. and Gait, M. J. (2012) *Peptide-mediated Cell and In Vivo Delivery of Antisense Oligonucleotides and siRNA*, Mol Ther Nucleic Acids, 1, e27]. Such methods can be employed to obtain the required drug distribution of the MO ASO.

The embodiments of the present invention recited herein are intended to be merely exemplary and those skilled in the art will be able to make numerous variations and modifications to it without departing from the spirit of the present invention. Notwithstanding the above, certain variations and modifications, while producing less than optimal results, may still produce satisfactory results. All such variations and modifications are intended to be within the scope of the present invention as defined by the claims appended hereto.

What is claimed is:

1. An antisense oligonucleotide having a nucleotide sequence that is complementary to a non-continuous portion of a sequence of intron 6, intron 7, or exon 7 of a survival motor neuron (SMN) 2 gene, the nucleotide sequence of the antisense oligonucleotide being chosen from [SEQ ID NO 1], [SEQ ID NO 2], [SEQ ID NO 4], [SEQ ID NO 5], [SEQ ID NO 6], [SEQ ID NO 7], [SEQ ID NO 8], [SEQ ID NO 9], [SEQ ID NO 10], [SEQ ID NO 11], [SEQ ID NO 12], [SEQ ID NO 13], and [SEQ ID NO 15];
wherein each nucleoside of the antisense oligonucleotide is linked to a morpholino ring.

2. The antisense oligonucleotide of claim 1, wherein morpholino rings are linked to one another via phosphorodiamidate groups.

3. The antisense oligonucleotide of claim 1, wherein the nucleotide sequence is targeted to a cis splicing regulatory element.

4. The antisense oligonucleotide of claim 3, wherein the cis splicing regulatory element is chosen from an exonic splicing enhancer, an exonic splicing silencer, an intronic splicing enhancer, and an intronic splicing silencer.

5. The antisense oligonucleotide of claim 3, wherein the cis splicing regulatory element is an intronic splicing silencer.

6. A method of incorporating exon 7 of the SMN2 gene into transcripts of the SMN2 gene, the method comprising:
administering to a subject an antisense oligonucleotide having a nucleotide sequence:
(i) that is chosen from [SEQ ID NO 1], [SEQ ID NO 2], [SEQ ID NO 4], [SEQ ID NO 5], [SEQ ID NO 6], [SEQ ID NO 7], [SEQ ID NO 8], [SEQ ID NO 9], [SEQ ID NO 10], [SEQ ID NO 11], [SEQ ID NO 12], [SEQ ID NO 13], and [SEQ ID NO 15]; or
(ii) which is sufficiently homologous to [SEQ ID NO 1], [SEQ ID NO 2], [SEQ ID NO 4], [SEQ ID NO 5], [SEQ ID NO 6], [SEQ ID NO 7], [SEQ ID NO 8], [SEQ ID NO 9], [SEQ ID NO 10], [SEQ ID NO 11], [SEQ ID NO 12], [SEQ ID NO 13], or [SEQ ID NO 15]
such that the nucleotide sequence of the antisense oligonucleotide is complementary to a non-continuous portion of a sequence of intron 6, intron 7, or exon 7 of the SMN2 gene.

7. The method of claim 6, wherein each nucleoside of the antisense oligonucleotide are linked to a morpholino ring.

8. The method of claim 7, wherein morpholino rings are linked to one another via phosphorodiamidate groups.

9. The method of claim 6, wherein the nucleotide sequence is targeted to a cis splicing regulatory element.

10. The method of claim 9, wherein the cis splicing regulatory element is chosen from an exonic splicing enhancer, an exonic splicing silencer, an intronic splicing enhancer, and an intronic splicing silencer.

11. The method of claim 9, wherein the cis splicing regulatory element is an intronic splicing silencer.

12. A composition for promoting the incorporation of exon 7 of the SMN2 gene into transcripts of the SMN2 gene, the composition comprising:
at least a first antisense oligonucleotide having a nucleotide sequence:
(i) that is chosen from [SEQ ID NO 1], [SEQ ID NO 2], [SEQ ID NO 4], [SEQ ID NO 5], [SEQ ID NO 6], [SEQ ID NO 7], [SEQ ID NO 8], [SEQ ID NO 9], [SEQ ID NO 10], [SEQ ID NO 11], [SEQ ID NO 12], [SEQ ID NO 13], and [SEQ ID NO 15]; or
(ii) which is sufficiently homologous to [SEQ ID NO 1], [SEQ ID NO 2], [SEQ ID NO 4], [SEQ ID NO 5], [SEQ ID NO 6], [SEQ ID NO 7], [SEQ ID NO 8], [SEQ ID NO 9], [SEQ ID NO 10], [SEQ ID NO 11], [SEQ ID NO 12], [SEQ ID NO 13], or [SEQ ID NO 15]
such that the nucleotide sequence of the antisense oligonucleotide is complementary to a non-continuous portion of a sequence of intron 6, intron 7, or exon 7 of the SMN2 gene; and
wherein each nucleoside of the antisense oligonucleotide is linked to a morpholino ring.

13. The composition of claim 12, further comprising a second antisense oligonucleotide.

14. The composition of claim 13, wherein the first antisense oligonucleotide and the second antisense oligonucleotide are each targeted to the same nucleic acid target.

15. The composition of claim 13, wherein the first antisense oligonucleotide and the second antisense oligonucleotide are each targeted to different nucleic acid targets.

* * * * *